(12) United States Patent
Hammer et al.

(10) Patent No.: US 10,571,539 B2
(45) Date of Patent: Feb. 25, 2020

(54) PATTERN ANALYSIS BASED ON FMRI DATA COLLECTED WHILE SUBJECTS PERFORM WORKING MEMORY TASKS ALLOWING HIGH-PRECISION DIAGNOSIS OF ADHD

(71) Applicant: Northwestern University, Evanston, IL (US)

(72) Inventors: Reuven Hammer, Evanston, IL (US); James R. Booth, Evanston, IL (US); Reza Borhani, Evanston, IL (US); Aggelos K. Katsaggelos, Evanston, IL (US)

(73) Assignee: Northwestern University, Evanston, IL (US)

( * ) Notice: Subject to any disclaimer, the term of this patent is extended or adjusted under 35 U.S.C. 154(b) by 450 days.

(21) Appl. No.: 15/317,724

(22) PCT Filed: Jun. 12, 2015

(86) PCT No.: PCT/US2015/035586
§ 371 (c)(1),
(2) Date: Dec. 9, 2016

(87) PCT Pub. No.: WO2015/192021
PCT Pub. Date: Dec. 17, 2015

(65) Prior Publication Data
US 2017/0123028 A1 May 4, 2017

Related U.S. Application Data

(60) Provisional application No. 62/011,427, filed on Jun. 12, 2014.

(51) Int. Cl.
*G01R 33/48* (2006.01)
*G16H 50/20* (2018.01)
(Continued)

(52) U.S. Cl.
CPC ........ *G01R 33/4806* (2013.01); *A61B 5/0042* (2013.01); *A61B 5/055* (2013.01);
(Continued)

(58) Field of Classification Search
CPC ..... A61B 5/0042; A61B 5/055; A61B 5/7235; A61B 5/7267; A61B 5/7282;
(Continued)

(56) References Cited

U.S. PATENT DOCUMENTS 7,567,693 B2    7/2009  deCharms
2005/0267357 A1  12/2005  Rao et al.
(Continued)

FOREIGN PATENT DOCUMENTS

WO    2015192021    12/2015

OTHER PUBLICATIONS

International Searching Authority, "Search Report", issued in connection with PCT patent application No. PCT/US15/35586, dated Sep. 21, 2015, 3 pages.
(Continued)

*Primary Examiner* — Edward Park
(74) *Attorney, Agent, or Firm* — Quarles & Brady LLP; Jonathan Stone

(57) ABSTRACT

Using a plurality of distinct behavioral tasks conducted in a functional magnetic resonance imaging (fMRI) scanner, fMRI data acquired from one or more subjects performing working memory tasks can be used for diagnosing psychiatrics and neurological disorders. A classification algorithm can be used to determine a classification model, tune the model, and apply the model. An output indicative of a subject's clinical condition can then be provided and used to diagnose new cases.

20 Claims, 15 Drawing Sheets

Schematics of the Visuospatial Working Memory Tasks and Scanning Procedure

(51) Int. Cl.
 *A61B 5/055* (2006.01)
 *A61B 5/00* (2006.01)
 *A61B 5/16* (2006.01)
 *G06T 7/00* (2017.01)
 *G06T 7/11* (2017.01)
 *G06K 9/46* (2006.01)

(52) U.S. Cl.
 CPC ............ *A61B 5/168* (2013.01); *A61B 5/7235* (2013.01); *A61B 5/7282* (2013.01); *G06K 9/4604* (2013.01); *G06T 7/0012* (2013.01); *G06T 7/11* (2017.01); *G16H 50/20* (2018.01); *A61B 2576/026* (2013.01); *G06T 2207/10088* (2013.01); *G06T 2207/30016* (2013.01)

(58) Field of Classification Search
 CPC .......... A61B 2576/026; G01R 33/4806; G06K 9/4604; G06K 9/6244; G06K 9/6256; G06T 7/0012; G06T 7/11; G06T 2207/10088; G06T 2207/30016; G16H 50/20
 See application file for complete search history.

(56) References Cited

U.S. PATENT DOCUMENTS

| | | | |
|---|---|---|---|
| 2006/0025673 A1* | 2/2006 | De Leon | G06T 7/0012 600/410 |
| 2008/0228686 A1* | 9/2008 | Fischer | A61B 5/055 706/46 |
| 2011/0092794 A1* | 4/2011 | Miller | A61B 5/103 600/407 |
| 2012/0143041 A1* | 6/2012 | Hirsch | A61B 5/055 600/411 |
| 2015/0018664 A1* | 1/2015 | Pereira | A61B 5/055 600/410 |

OTHER PUBLICATIONS

International Searching Authority, "Written Opinion", issued in connection with PCT patent application No. PCT/US15/35586, dated Sep. 21, 2015, 5 pages.
Sato Jr. et al, "Evaluation of pattern recognition and feature extraction methods in ADHD prediction", Frontiers in Systems Neuroscience, Sep. 24, 2012., vol. 6. Article 68, 14 pages.
Kawano et al,"Identifying Gene Pathways Associated with Cancer Characteristics via Sparse Statistical Methods" IEEEIACM Transactions on Computational Biology and Bioinformatics, Jul. 27, 2012. vol. 9.4: 966-72; Abstract, 2 pages.
International Bureau, "International Preliminary Report on Patentability", issued in connection with PCT patent application No. PCT/US2015/035586, dated Dec. 22, 2016, 7 pages.
Anderson et al., "Non-negative matrix factorization of multimodal MRI, fMRI and phenotypic data reveals differential changes in default mode subnetworks in ADHD", retrieved from journal homepage: www.elsevier.com/locate/ynimg, NeuroImage 102 (year 2014) 207-219, 13 pages.
Guiassian et al., "Learning to Classify Psychiatric Disorders based on fMR Images: Autism vs Healthy and ADHD vs Healthy", 2013, 7 pages.
Hart et al., "Predictive Neurofunctional Markers of Attention-Deficit/Hyperactivity Disorder Based on Pattern Classification of Temporal Processing", 2014 Journal AA of Child & Adolescent Psychiatry, 11 pages.
Hart et al., "Pattern Classification of Response Inhibition in ADHD: Toward the Development of Neurobiological Markers for ADHD", 2014 Human Brain Mapping 35:3083-3094, 12 pages.
Iannaccone et al, "Classifying adolescent attention-deficit/hyperactivity disorder (ADHD) based on functional and structural imaging", published on Jan. 23, 2015, Eur Child Adolesc Psychiatry (2015) 24:1279-1289, 11 pages.

Lenartowics et al., "Use of EEG to Diagnose ADHD", published Sep. 20, 2014, Curr Psychiatry Rep (2014) 16:498, 11 pages.
Quresshi et al., "Multiclass Classification for the Differential Diagnosis on the ADHD Subtypes Using Recursive Feature Elimination and Hierarchical Extreme Learning Machine: Structural MRI Study", Aug. 8, 2016, PLoS One 11(8):e0160697. doi:10.1371/journal.pone.0160697, 20 pages.
Lim et al., "Disorder-Specific Predictive Classification of Adolescents with Attention Deficit Hyperactivity Disorder (ADHD) Relative to Autism Using Structural Magnetic Resonance Imaging", PLOS One | www.plosone.org, May 2013, vol. 8, Issue 5, 10 pages.
Rosa et al, "Sparse network-based models for patient classification using fMRI", retrieved from journal homepage: www.elsevier.com/locate/ynimg, NeuroImage 105 (2015) 493-506, 14 pages.
Sidhu et al., "Kernel Principal Component Analysis for dimensionality reduction in fMRI-based diagnosis of ADHD", Frontier in Systems Neuroscience, Nov. 9, 2012, https://doi.org/10.3389/fnsys.2012.00074, 16 pages.
Sundermann et al., "Multivariate Classification of Blood Oxygen Level—Dependent fMRI Data with Diagnostic Intention: A Clinical Perspective", retrieved from www.ajnr.org, May 2014, 8 pages.
Wolfers et al., "Quantifying patterns of brain activity: Distinguishing unaffected siblings from participants with ADHD and healthy individuals", retrieved from journal homepage: www.elsevier.com/locate/ynimg, NeuroImage: Clinical 12 (2016) 227-233, 7 pages.
Anderson A, et al. Non-negative matrix factorization of multimodal MRI, fMRI and phenotypic data reveals differential changes in default mode subnetworks in ADHD. NeuroImage. 2014.
Burgess GC, et al. Attentional control activation relates to working memory in attention-deficit/hyperactivity disorder. Biol Psychiatry. 2010;67(7):632-40. doi: 10.1016/j .biopsych.2009.10.036.
Cawley GC, et al. Gene selection in cancer classification using sparse logistic regression with Bayesian regularization. Bioinformatics. 2006;22(19):2348-2355. doi: 10.1093/bioinformatics/btl386.
Ehlis AC, et al. Reduced lateral prefrontal activation in adult patients with attention-deficit/hyperactivity disorder (ADHD) during a working memory task: A functional near-infrared spectroscopy (fNIRS) study. J Psychiatr Res. 2008;42(13): 1060-1067.
Fair DA, et al. Distinct neural signatures detected for ADHD subtypes after controlling for micro-movements in resting state functional connectivity MRI data. Front Syst Neurosci. 2012a;6:80. doi: 10.3389/fnsys.2012.00080.
Hart H, et al. Meta-analysis of fMRI studies of timing in attention deficit hyperactivity disorder (ADHD). Neurosci Biobehav Rev. 2012;36(10):2248-2256.
Koh K, et al. An Interior-Point Method for Large-Scale LI-Regularized Logistic Regression. J Mach Learn Res. 2007;8:1519-1555. doi:10.1.1.88.5451.
Lim L, et al. Disorder-Specific Predictive Classification of Adolescents with Attention Deficit Hyperactivity Disorder (ADHD) Relative to Autism Using Structural Magnetic Resonance Imaging. PLoS One. 2013;8(5).
Ma S, et al. Penalized feature selection and classification in bioinformatics. Brief Bioinform. 2008;9(5):392-403.
Orru G, et al. Using Support Vector Machine to identify imaging biomarkers of neurological and psychiatric disease: a critical review. Neurosci Biobehav Rev. 2012;36(4): 1140-52. doi: 10.1016/j.neubiorev.2012.01.004.
Peng X, et al. Extreme learning machine-based classification of ADHD using brain structural MRI data. PLoS One. 2013;8(11).
Ryali S, et al. Sparse logistic regression for whole-brain classification of fMRI data. Neuroimage. 2010;51(2):752-64. doi: 10.1016/j.neuroimage.2010.02.040.
Schmidt M. Graphical Model Structure Learning with LI-Regularization. PhD thesis, University of British Columbia. 2010.
Wong G, et al. FSR: feature set reduction for scalable and accurate multiclass cancer subtype classification based on copy number. Bio informatics. 2012;28(2): 151-159. doi: 10.1093/bioinformatics/btr644.
Wu TT, et al. Genome-wide association analysis by lasso penalized logistic regression. Bio informatics. 2009;25(6):714-721.

(56) References Cited

OTHER PUBLICATIONS

Zhu CZ, et al. Fisher discriminative analysis of resting-state brain function for attention-deficit/hyperactivity disorder. Neuroimage. 2008;40(1): 110-120.

* cited by examiner

First-Phase Classification

Second-Phase K ≥ 10 Model
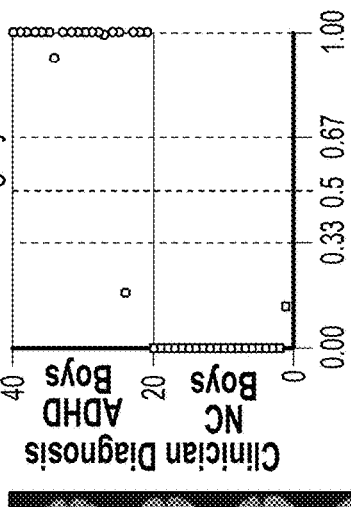
FIG. 2F
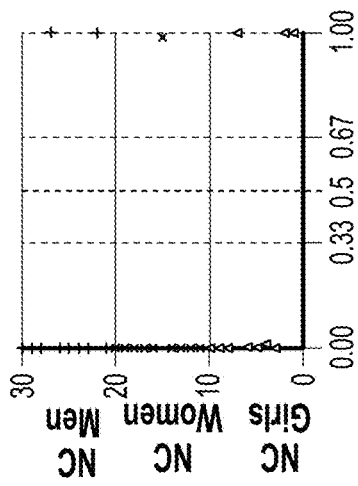
FIG. 2G
Second-Phase K ≥ 20 Model
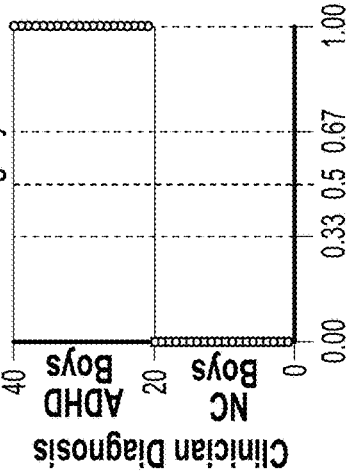
FIG. 2I
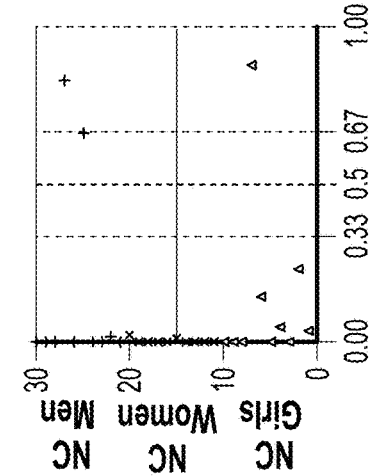
FIG. 2J
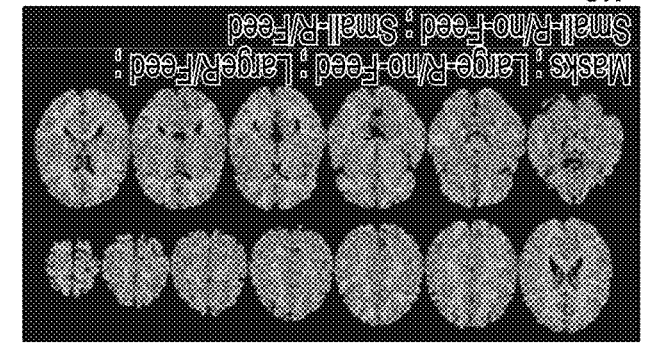
FIG. 2E / FIG. 2H
Masks: Large-R/no-Feed ; Large-R/Feed ; Small-R/no-Feed ; Small-R/Feed

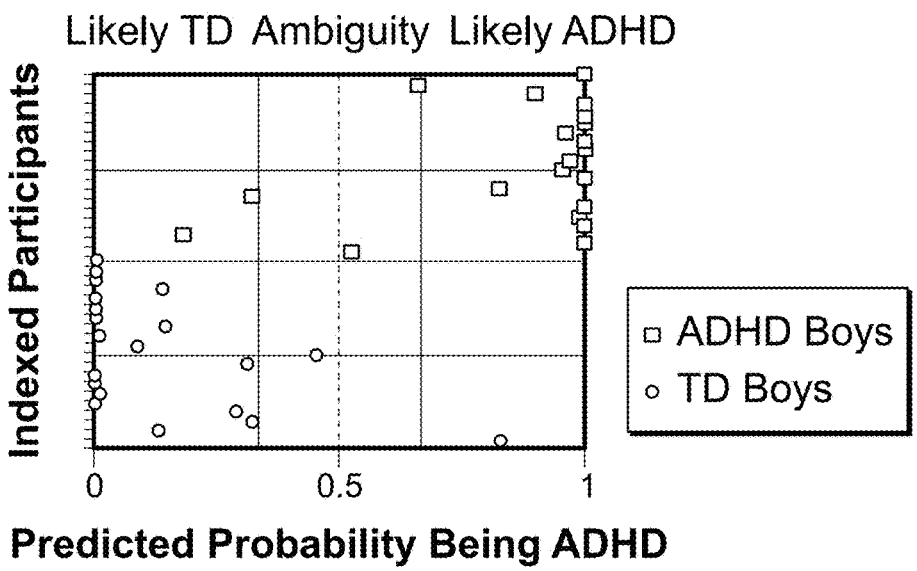
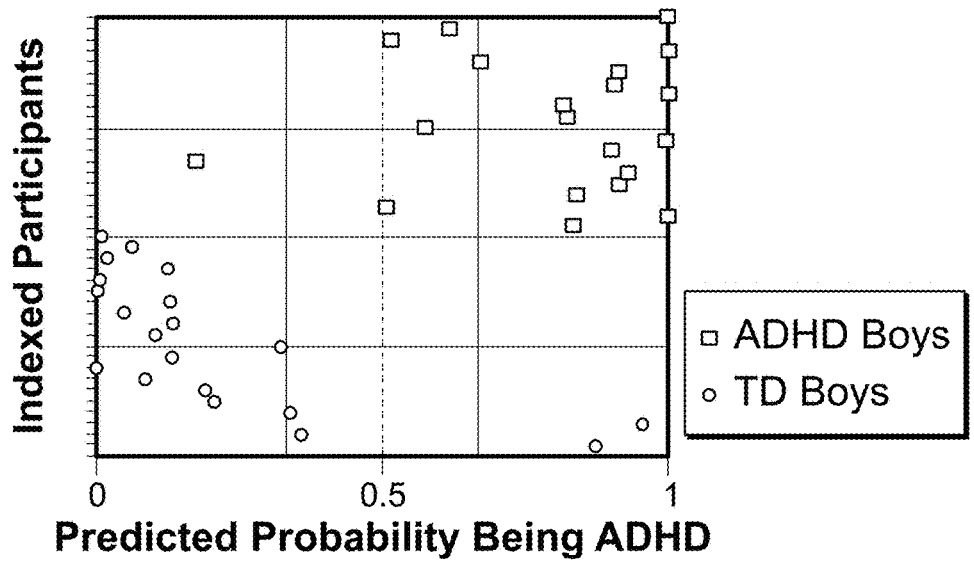
FIG. 11

PATTERN ANALYSIS BASED ON FMRI DATA COLLECTED WHILE SUBJECTS PERFORM WORKING MEMORY TASKS ALLOWING HIGH-PRECISION DIAGNOSIS OF ADHD

CROSS-REFERENCE TO RELATED APPLICATIONS

This patent arises from the U.S. national stage of International Patent Application Serial No. PCT/US15/35586, having an International Filing Date of Jun. 12, 2015, and claims priority to U.S. Provisional Application Ser. No. 62/011,427, entitled "Pattern Analysis Based on fMRI Data Collected While Subjects Perform Working Memory Tasks Allowing High-Precision Diagnosis of ADHD," which was filed on Jun. 12, 2014, both of which are hereby incorporated herein by reference in its entirety for all purposes.

STATEMENT REGARDING FEDERALLY SPONSORED RESEARCH OR DEVELOPMENT

This invention was made with government support under R21 MH080820 awarded by the National Institutes of Health. The government has certain rights in the invention.

FIELD OF THE DISCLOSURE

This disclosure relates generally to multivariate neuroimaging data analysis and, more particularly, to use of functional Magnetic Resonance Imaging data (fMRI) collected while subjects perform an ensemble of a few behavioral working memory tasks.

BACKGROUND

The statements in this section merely provide background information related to the disclosure and may not constitute prior art.

Neuroimaging techniques, such as magnetic resonance imaging, can be used to aid in diagnosis of neuropsychiatric disorders. Identifying neurobiological markers of neurodevelopmental disorders, such as Attention Deficit and Hyperactivity Disorder (ADHD) (including attention deficit disorder (ADD)), is an objective of clinicians and neuroscientists. Current efforts, however, have not proven to be effective or useful, due to heterogeneities within the clinical and normal populations, evident also in their structural brain images, and in functional brain images that may exhibit task related activity or resting-state activity. These heterogeneities make the task of identifying the brain regions that best characterize the clinical population most challenging.

BRIEF SUMMARY

Certain examples provide systems, methods, and apparatus to monitor and model subjects performing working memory tasks. Certain examples provide high-precision diagnosis of ADHD.

An example method includes receiving, using a configured processor, functional neuroimage data of a subject acquired while the subject performs a series of working memory tasks. The neuroimage data includes clusters of voxels representing regions of brain activity. Some regions are activated and some regions are deactivated during performance of the series of working memory tasks. The example method includes extracting, using the configured processor, for a plurality of regions of interest in the neuroimage data, a mean activity level in each of the series of working memory tasks. The example method includes determining, using the configured processor, brain activation based on the cluster of voxels corresponding to each of the plurality of regions of interest. The brain activation for each region of interest is identified as a feature. The example method includes reducing, using the configured processor, the features using a sparse principal component analysis to generate a number of orthogonal principal components smaller than the number of original features. Each of the principal components corresponds to a combination of features. The example method includes applying, using the configured processor, a logistic regression classification to the principal components based on a classification model for Attention Deficit and Hyperactivity Disorder (ADHD). The example method includes outputting, using the configured processor, a predicted probability of ADHD based on the logistic regression classification.

Certain examples provide a tangible machine readable medium having instructions stored thereon, which when executed, cause a machine to implement a method, The example method includes receiving functional neuroimage data of a subject acquired while a subject performs a series of working memory tasks. The neuroimage data includes clusters of voxels representing regions of brain activity. Some regions are activated and some regions are deactivated during performance of the series of working memory tasks. The example method includes extracting, for a plurality of regions of interest in the neuroimage data, a mean activity level in each of the series of working memory tasks. The example method includes determining brain activation based on the cluster of voxels corresponding to each of the plurality of regions of interest. The brain activation for each region of interest is identified as a feature. The example method includes reducing the features using a sparse principal component analysis to generate a number of orthogonal principal components less than the number of features. The principal components correspond to a combination of features. The example method includes applying a logistic regression classification to the principal components based on a classification model for Attention Deficit and Hyperactivity Disorder (ADHD). The example method includes outputting a predicted probability of ADHD based on the logistic regression classification.

BRIEF DESCRIPTION OF THE DRAWINGS

FIGS. 2A-2J show example output. FIGS. 2A-2D show a collection of fMRI data and a first-phase classification of voxels from the fMRI images. FIGS. 2E-2J show a second-phase voxel cluster selection and model retesting.

FIG. 11 provides an example of ADHD classification accuracies as a predicted probability of a subject being an ADHD case.

Figure 1:
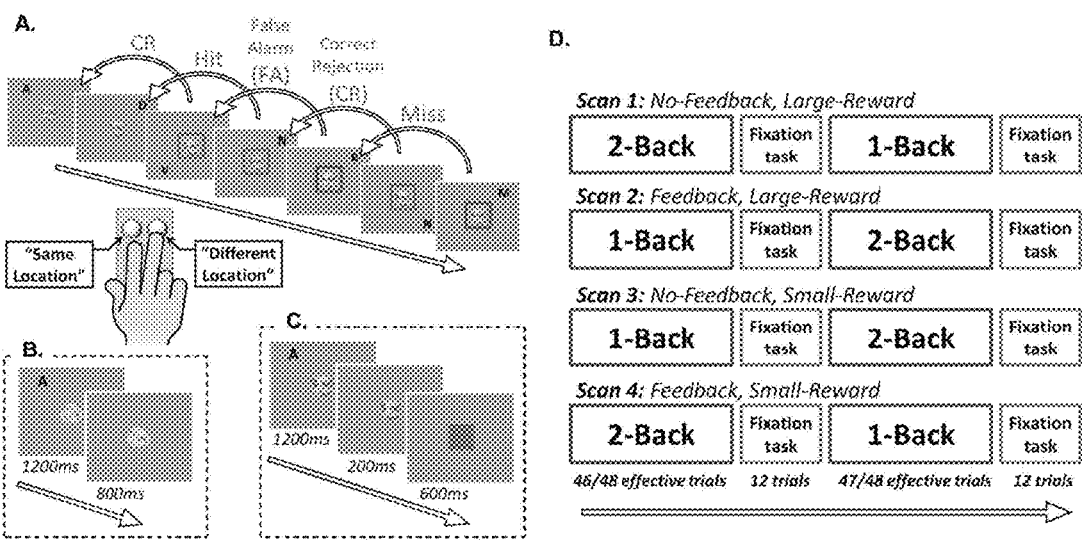
FIG. 1 depicts an example showing a plurality of visuospatial working memory tasks and associated scanning procedure
Figure 2A:
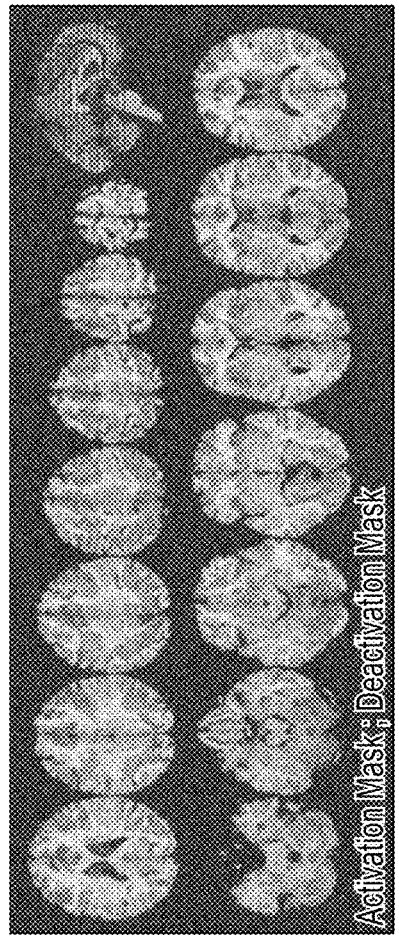
Figure 2B:
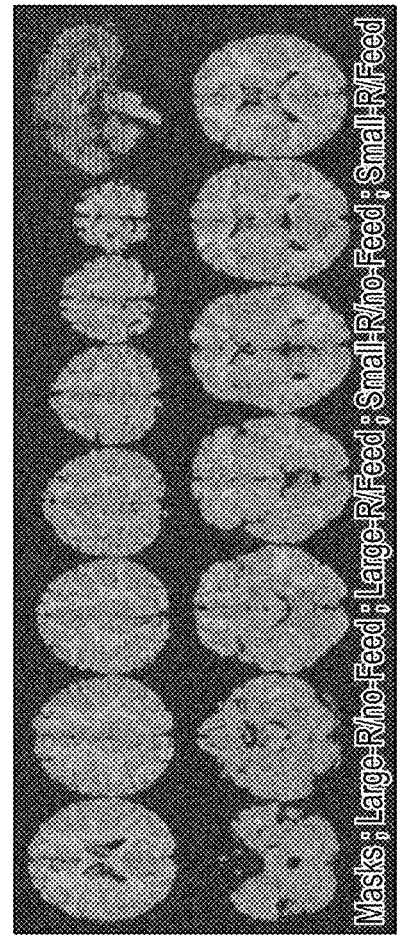
Figure 2C:
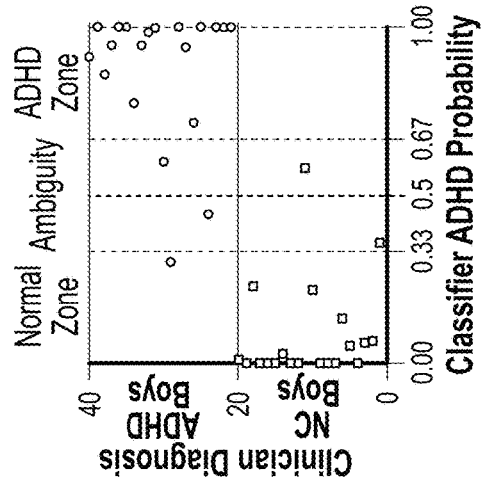
Figure 2D:
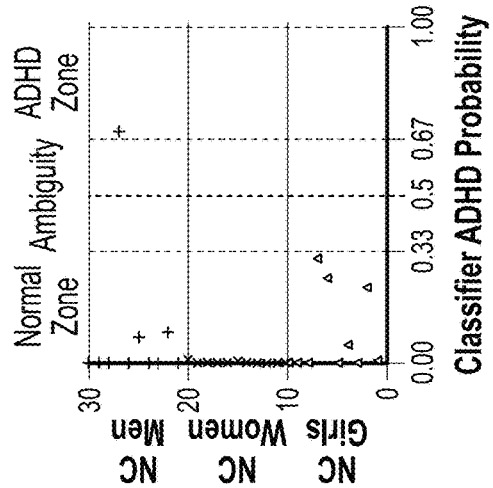

The following detailed description of certain embodiments of the present invention will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

Identifying neurobiological markers of neurodevelopmental disorders, such as Attention Deficit and Hyperactivity Disorder (ADHD), is a challenging objective of clinicians and neuroscientists. ADHD is characterized by multiple cognitive deficits associated with context dependent abnormal patterns of neural activity distributed across multiple brain regions. ADHD is unlikely to be characterized by localized structural brain abnormalities robust enough to be detected using available structural imaging techniques. It is also unlikely that significant functional brain abnormalities characterizing ADHD would be evident regardless of the mental state of the test subject during a scan.

Characteristics of ADHD include poor working memory, greater reliance on external feedback, and abnormal reward processing. These characteristics are associated with altered patterns of activity in distinct brain networks: (i) attention and working memory including the dorsolateral prefrontal cortex, parietal cortex, and temporal cortices; (ii) executive functions and cognitive control (e.g., including feedback processing and response selection) including the dorsal, medial and ventral frontal cortices; and (iii) reward processing including the orbitofrontal cortex, anterior cingulate cortex, and basal ganglia.

Children with ADHD have been reported to exhibit altered patterns of brain activity in several brain networks, conditioned by the characteristics of the performed tasks. This includes altered brain activity in working memory, reward processing and feedback processing networks. In certain examples, children with ADHD and children with normal brain activity (e.g., normal controls) are tested on an ensemble of tasks tapping into key neurocognitive deficits in ADHD. Monitoring of the children while there are performing these tasks highlights an increase in difference in patterns of neural activity between children with ADHD and Normal Controls (NC). This difference in neural activity pattern between children with ADHD and NC children helps facilitate higher accuracies in diagnosing ADHD using functional neuroimaging data collected while participants perform these tasks.

For example, participants can be tested in a plurality (e.g., four) of distinct visuospatial working memory tasks performed by the participants in a functional Magnetic Resonance Imaging (fMRI) scanner. Using fMRI data from an ensemble of VisuoSpatial Working Memory (VSWM) tasks that differ in motivational context (e.g., determined by availability of reward and/or feedback, etc.) can increase odds that abnormal patterns of brain activity are reliably detected in a larger proportion of ADHD cases. For example, tasks orthogonally vary in feedback availability (e.g., no-feedback, feedback) and reward size (e.g., large, small). Execution of VSWM tasks can be measured and compared to execution of fixation tasks (e.g., a baseline, repeated rote task) by the same subjects.

Using independent univariate analysis, multiple brain regions of interest can be identified and later be used in a multimodal analysis. Using a sparse principal component analysis, a number of variables describing each subject can be reduced prior to being provided as input to a classifier. For ADHD diagnosis, an fMRI multivariate analysis can be conducted using a Sparse Logistic Regression (SLR) and/or other Logistic Regression (LR) classification algorithm that receives as input the fMRI data acquired while boys performed four working memory tasks (e.g., four tasks involving tracking spatial location of letters while ignoring the letters' identity and executing timely responses, etc.). SLR can be used to replace the variables reduction phase done by the sparse principle component analysis. The manipulation of feedback and reward provide different motivational contexts, each involving somewhat distinct executive skills found to be impaired in children with ADHD. The (S)LR algorithm is designed to search for an optimized classification model, based only on the most informative voxel-clusters. The (S)LR classifier can model class conditional probabilities for each case (e.g., calculating a predicted probability that a given child has ADHD) while attempting to find a model allowing a decisive classification of as many cases as possible.

Cross-validation test shows that a classification model determined by the (S)LR classifier allows highly accurate and decisive classification and diagnosis, indicating low susceptibility to overfitting (e.g., modeling too specifically to include random, non-reproducible relationships among data) and confounds (e.g., factors that distort a true relationship between variables of interest). Accurate diagnosis is also preserved when the (S)LR classifier processes morphed and noisy fMRI images, simulating potentially more ambiguous cases. Thus, certain examples use fMRI to provide a reliable psychiatric diagnostic tool. Similar principles and methodologies can be used to diagnose other psychiatric and neurological disorders for which there are no available reliable objective diagnostic tools (to include differentiating between subtypes of ADHD, diagnosing learning disorders, autism or early onsets of aging related neural disorders, for example).

This disclosure relates generally to multivariate neuroimaging data analysis and, more particularly, to use of functional Magnetic Resonance Imaging data (fMRI) collected while subjects perform an ensemble of a few behavioral working memory tasks. Such a use of few tasks improves the capacity of detecting abnormal patterns of neural activity characterizing cognitive and psychiatric disorders, while better accounting to unimportant individual differences (e.g., within the normal population or the clinical population) in contrast to the important difference between the normal population and the clinical population, and between subgroups within the clinical population.

The examples disclosed herein provide systems and methods, which use several distinct behavioral tasks that tap into cognitive abnormalities in a clinical population and thus increase the chance that patterns of neural activity distinct to the targeted clinical population will be triggered more effectively. In certain scenarios, since both the target clinical population and a normal patient population are heterogeneous, no single task is likely to be sufficient in triggering altered neural activity in all patients. Thus, using multiple tasks allows a classification algorithm to better capture core differences between patient populations or clinical subgroups and to discard irrelevant individual differences within each group. Certain examples use an ensemble of few functional brain images (e.g., function magnetic resonance image (fMRI) or other neuroimaging technique for measuring brain activity, for example by detecting changes in blood oxygenation and flow occurring in response to neural activity), each acquired under a distinct behavioral manipulation (distinct behavioral tasks conducted by the participants), as an input for the classification algorithm.

Alternatively or in addition to the systems and methods disclosed above, certain examples disclosed herein provide a diagnostic tool including dual-phase model detection followed by a model-tuning procedure. In the first phase a Sparse Logistic Regression (SLR) classifier is used to detect voxels in a brain image that are most informative in dissociating between patient subjects and normal (e.g., non-patient) subjects. In a second phase, voxels that are clustered together in smaller-voxel clusters are excluded from the model, and a logistic regression classifier is applied again in order to recalculate the respective weights of the remaining voxels. For example, in the second phase, voxels that are clustered together in clusters with ten (10) voxels or more are kept. Since individual brains have distinct morphologies, which impact the respective spatial coordinates of abnormal patterns of activity, restricting a model to only larger voxel-clusters reduces the chance that the ADHD diagnosis model determined by the sparse logistic regression (SLR) classifier will be spatially over-fitted (based on restrictive spatial template). After the exclusion of the voxels in smaller clusters, a logistic regression classifier (a variation of the sparse logistic regression classifier, with no sparsity) is re-applied to update respective weights of the remaining voxels, forcing the inclusion of all these remaining voxels (e.g., voxels in the K≥10 clusters).

In certain cases, clinicians using the diagnostic tool can upload fMRI images acquired during a diagnosis procedure to a server that runs the classification algorithm. The ongoing input of images from new subjects (both clinical and normal) allows continued updating and tuning of an ADHD classification model and improvement of future variations of the diagnosis procedure. When a clinician provides additional information about a patient, application of the classification algorithm to that patient can be reviewed to determine of the algorithm was miss-detecting or false-detecting an ADHD case. Such a continued updating allows the system to increase its diagnosis accuracy, making the diagnostic procedure incrementally more reliable.

II. Example Analysis Systems and Methods

Developing a reliable and objective diagnostic procedure for ADHD is of great importance, as ADHD affects 5-8% of the worldwide childhood population, has high comorbidity and shares symptoms with other behavioral and emotional disorders. A recent major concern is the marked variability in diagnostic rates of ADHD in the US and marked increase in its diagnosis rate worldwide, especially among those who live in high-income households, and in older age. For example, according to the Center for Disease Control and Prevention, 11% of children in the US were diagnosed with ADHD in 2011 versus 7.8% in 2003. This may reflect higher awareness and an increased sensitivity of schoolteachers and parents to symptoms of ADHD. Yet evidence suggests that this trend indicates a bias in the current descriptive (e.g., symptom-based) diagnostic procedure. Furthermore, recent changes in Diagnostic and Statistical Manual (DSM V) criteria are likely to result in more individuals being diagnosed with ADHD, as age of onset criteria have been increased. Clearly, much needs to be done to improve screening, diagnosis and treatment for ADHD.

As Magnetic Resonance Imaging scanners become more available, researchers and clinicians strive to discover neuroimaging-based biomarkers that will improve diagnosis of psychiatric and neurological disorders. Nevertheless, previous attempts to diagnose ADHD using structural imaging, resting-state fMRI, fMRI data acquired during cognitive tasks, or combinations of these techniques, resulted in diagnosis accuracies significantly above chance, but far from meeting criteria for reliable ADHD diagnosis: Most studies either show too low overall classification accuracy and/or a significant diagnostic bias, and they all fail to report highly confident, reproducible, diagnostic decisions at an individual level.

A major challenge in diagnosing ADHD (and most other psychiatric disorders) is heterogeneities found within clinical and normal populations, evident also in their MRI/fMRI brain images. One major source of heterogeneity is a large variability in structural characteristics of the human brain. These structural variabilities are evident in global volume and shape, as well as more local features such as cortical thickness in specific regions, or axonal projections between specific regions. This variability compromises a capacity to associate a psychiatric disorder with unique structural characteristics that can be reliably detected using available techniques. In addition to underlying structural heterogeneities that may impact acquired functional data, resting-state fMRI is sensitive to contextual factors. For example, similarities between patterns of resting-state fMRI of a patient versus a normal subject may increase if they both experience discomfort, fatigue or anxiety during the scanning session. This may overshadow resting-state activation patterns characterizing the targeted clinical population. Diagnosing based on fMRI data acquired during a single cognitive task can be effective when there is a straightforward association between the cognitive task and the targeted disorder, for example when using a phonological task for diagnosing reading disabilities. Nevertheless, such a diagnosis procedure is less effective when the targeted disorder is characterized by several behavioral symptoms, where none of these symptoms is both necessary and sufficient for determination of a clinical diagnosis. Each of the above sources of heterogeneities compromises efforts to discover reliable neurobiological markers.

Evidence suggests that ADHD is characterized by multiple deficits associated with context dependent abnormal patterns of neural activity distributed across multiple brain regions. Key cognitive characteristics of ADHD include poor working memory, an increased reliance on external feedback, and abnormal reward processing. Each of these characteristics is associated with altered patterns of neural activity in distinct networks: (i) Attention and working memory networks, including dorsolateral prefrontal cortex, parietal cortex and temporal cortices; (ii) Executive function networks including dorsal, medial and ventral prefrontal cortices; and (iii) Dopamine based reward-processing networks, including orbitofrontal cortex, anterior cingulate cortex and basal ganglia.

Example Data Capture

In certain examples, fMRI data is acquired while children perform a plurality of (e.g., four) distinct visuospatial working memory (VSWM) tasks, and the acquired fMRI data is used as an input to a Sparse Logistic Regression (SLR) classification algorithm. The VSWM tasks differed from one another in the availability of trial-by-trial feedback (e.g., no-feedback vs. feedback) and the participant's expectation for monetary reward (e.g., large vs. small). That is, each of the VSWM tasks has a distinct set of cognitive demands associated with reward or feedback processing. For each participant, cumulative head movement is calculated as cumulative movement during a scanning session (e.g., summing an absolute value of movements on a frame-by-frame basis), and the maximal displacement e.g., a distance between two distant images) in each axis.

An ensemble of tasks tapping into key neurocognitive deficits in ADHD can substantially increase differences in patterns of neural activity between the ADHD group and normal controls. This helps improve a capacity to discard irrelevant variability in patterns of neural activity, allowing the SLR classifier to diagnose ADHD with higher precision.

FIG. 1 depicts an example showing a plurality of visuospatial working memory tasks and associated scanning procedure, for example. As shown in the example of FIG. 1, section (A) illustrates several trials in a 2-back task with large-reward and trial-by-trial feedback. Participants are provided with two keys in a response box. Four possible responses are provided: (i) Hit—correctly detecting that a location of a current letter is identical to a location of a 2-back letter; (ii) Correct Rejection (CR)—correctly detecting that the location of the current letter is different from the location of the 2-back letter; (iii) False Alarm (FA)—incorrectly responding that the location of the current letter is identical to the location of the 2-back letter; and (iv) Miss—incorrectly responding that the location of the current letter is different from the location of the 2-back letter when it is actually the same.

Section (B) of FIG. 1 illustrates a single trial in a small-reward (e.g., symbolized to participants using a picture of coins) no-feedback task. For example, a letter is presented for 1200 milliseconds followed by an 800 millisecond presentation of the coin reward-size symbol. Section (C) of FIG. 1 shows a single trial in a large-reward (e.g., symbolized to participants using a picture of dollar bills) trial-by-trial feedback task. A letter presentation of 1200 milliseconds is followed by a 200 millisecond presentation of the dollar reward-size symbol, for example. Section (D) of FIG. 1 illustrates an example series of four scans during four VSWM tasks over a plurality of trials.

Working Memory n-Back Tasks

Certain examples aid in diagnosis of a clinical condition in one or more subjects. For example, functional neuroimages (e.g., fMRIs) are obtained of one or more subject brains as tasks are performed. In certain examples, participants perform a modified n-back task (e.g., four modified 2-back tasks, etc.) while being scanned in an fMRI scanner. In each scan, the participants perform a task (e.g., 48 trial long 2-back task and a corresponding 48 trial long 1-back task, where the order of the two can be counterbalanced). Each n-back task is preceded and/or followed by a fixation task in which participants are asked to press a key whenever the fixation-cross changes its color. Each of these tasks is organized in a separate block of trials. Brain activity from the fixation tasks is used as a baseline for identifying brain regions responsive to the working memory manipulation. Software, such as E-Prime® 2.0 (sold by Psychology Software Tools, Inc.) can be used for stimuli presentation and for recording participant responses, for example.

In certain examples, two independent variables examined are reward size (e.g., large reward vs. small reward) and presence of trial-by-trial feedback (e.g., no feedback vs. feedback). In some examples, subjects can be instructed that a reward for each correct decision in a large-reward task is ten times larger than in a small-reward task. In certain examples of a trial-by-trial feedback task, each key press can be followed by either a green square (e.g., indicating a correct decision) or a red square (e.g., indicating an incorrect decision) presented to the subject (e.g., via a user interface). In certain examples, in a no-feedback task, the subject is not informed above his or her performance until after the task is completed.

MRI and fMRI Data Acquisition

Image data can be acquired using an MRI scanner. Gradient echo localizer images can also be acquired to determine placement of functional slices, for example. A susceptibility weighted single-shot EPI (Echo planar imaging) method with BOLD (blood oxygenation level-dependent) can be used for functional image acquisition, for example. Slices can be acquired in an interleaved manner, and a high resolution 3D image can also be obtained. In certain examples, to reduce or minimize head movements in the scanner, gaps between a subject's head and the scanner's head coil can be filled with foam (e.g., memory foam).

Image Preprocessing

Data preprocessing and/or analysis can be performed using available tools such as SPM8 (Statistical Parametric Mapping, Welcome Trust Centre for Neuroimaging, London, UK), MathWorks® Matlab, SPM8 (Statistical Parametric Mapping, Welcome Trust Centre for Neuroimaging, London, UK), IBM® SPSS, and/or specifically adjusted variations of these tools. fMRI image preprocessing can involve slice timing, realignment of functional images (e.g., to the $24^{th}$ image), co-registration of functional and anatomical images, and normalization of image(s) to a template or reference image, for example. Linear and non-linear normalization parameters can then be applied to the functional images. Images with movement artifacts (e.g., up to 9 per scan) can be replaced using interpolated values from two adjacent non-outlier volumes. In subsequent general linear model (GLM) analysis, excluded noisy volumes can be de-weighted, for example.

Feature Detection and Dimensionality Reduction

In certain examples, features are detected and dimensionality reduced. Feature selection can be based on a univariate GLM analysis (e.g., using standard analysis tools such as BrainVoyager™ by Brain-Innovation, or SPM8 by the Wellcome Trust Centre for Neuroimaging, etc.). FIGS. 2A-2D show example output including a collection of fMRI data and a first-phase classification of voxels from the fMRI images. FIGS. 2E-2J show an example output including a second-phase voxel cluster selection (e.g., based on minimal cluster size) and model retesting), for example, intended to identify functional brain regions of interest (fROIs) each including a cluster of a plurality of correlated voxels that show significant activation or deactivation in VSWM tasks (e.g., all four VSWM tasks) in contrast to fixation tasks. In certain examples, eight fROIs show significant activation (VSWM>fixation) and eight fROIs showing significant deactivation (fixation>VSWM). The sixteen fROIs reflect the VSWM network in a broad childhood population in varying contexts.

For each participant, a contrast or difference in mean Beta values is calculated between each VSWM task (e.g., 2-back, 1-back, . . . n-back) and mean of fixation tasks performed within the same scan, or all the fixation tasks conducted during the scanning session. These modeled and contrasted fMRI images are used as the input to an LR/SLR classifier for pattern analysis, where each voxel or cluster of voxels from each fMRI image is considered as a feature. For example, given four VSWM tasks and sixteen fROIs, an initial number of features is 64.

Given a relatively large initial number of features (e.g., 64) and high correlations between some of the features, dimensionality of the data can be reduced using a sparse principal component analysis (SPCA). A reduction using SPCA results in a relatively small number of orthogonal principal components (PCs), where each PC can be recalculated based only on a few features with highest loadings.

Using SPCA, a number of variables fed into a classifier can be reduced to a number substantially smaller than a number of subjects in the imaging analysis. Additionally, recalculating PCs based only on features with highest loadings enables exclusion of lower weight features that are likely to add mostly noise. Further, having each PC be affected by relatively few features, wherein each feature affects at most one PC, enables better determination of underlying neurocognitive mechanisms represented by each PC.

For example, using a sparse loadings selection based on thresholding of rotated loadings (e.g., based on a Varimax rotation method) results in 39 features (out of 64 available features) that affect a first 10 PCs, in which each feature affects a single PC. In certain examples, the first 10 PCs explain approximately 70% of variability evident in the original 64 features described above. Each of the remaining PCs explain less than 3% of the variability in the data. Each of the first 10 PCs reflects brain activity from several ROIs from the same VSWM task but not brain activity in a specific ROI in several tasks. This is an indication that functional brain imaging data from several distinct tasks adds information useful for classification of a condition such as ADHD, as compared to the use of a single task.

Pattern Analysis Using a Logistic Regression Classifier

In certain examples, in a first phase, a model, which is based on the most informative PCs (see SPCA above), is determined. For example, a Logistic Regression (LR) classifier can be used to discriminate between two (or more) classes of interest. For example, the first 10 PCs can be fed into an LR classifier as input variables. In the example, entering the 10 PCs into the LR classification model results in high accuracy (e.g., 92.5%), high sensitivity (e.g., 90% correct classification of ADHD boys), and high specificity (e.g., 95% correct classification of typically developed (TD) boys) for accurate and decisive classification decisions with high predicted ADHD probability values.

Alternatively or in addition, a leave-one-out cross validation (referred to as a 'jackknife') can be used to find a classification model that is less likely to be overfitted. In each cross validation iteration, the LR classifier can be trained based on the fMRI data, and then a goodness fit of the learned model can be evaluated based on a correlation between the clinical diagnosis of a left-out subject (e.g., ADHD or TD) and the LR classifier-predicted ADHD probability for the subject, repeated for each subject. A predictive power from all iterations can be averaged to determine which of the ten PCs has statistically significant predictive power and to estimate a predictive power of the final model. In an example, four PCs can be identified as having a statistically significant contribution for ADHD classification.

A variant of this classification algorithm, referred to as Sparse Logistic Regression (SLR), can be effectively used in bioinformatics analysis where high dimensionality of data may hinder effective feature selection, and a relatively small number of samples makes other classifiers susceptible to overfitting. SLR addresses both these issues by a regularization term to the classic Logistic Regression model. This regularization term is used to enforce sparsity on a weights vector, where each entry of the vector can be interpreted as a contribution of its corresponding feature (voxel) in determining a final classification decision. Voxels with weight of zero are discarded from the model, thus resolving a feature selection problem as part of a model discovery process. A number of non-zero weights, or the number of selected voxels, is controlled by a parameter $\lambda$ determining a trade-off between a degree of feature/voxel pruning (e.g., sparsity) and classification accuracies (e.g., logistic loss). These attributes make the SLR classification algorithm a valuable tool for a whole brain level MRI/fMRI pattern analysis.

Dual-Phase Classification Example

Figure 3:
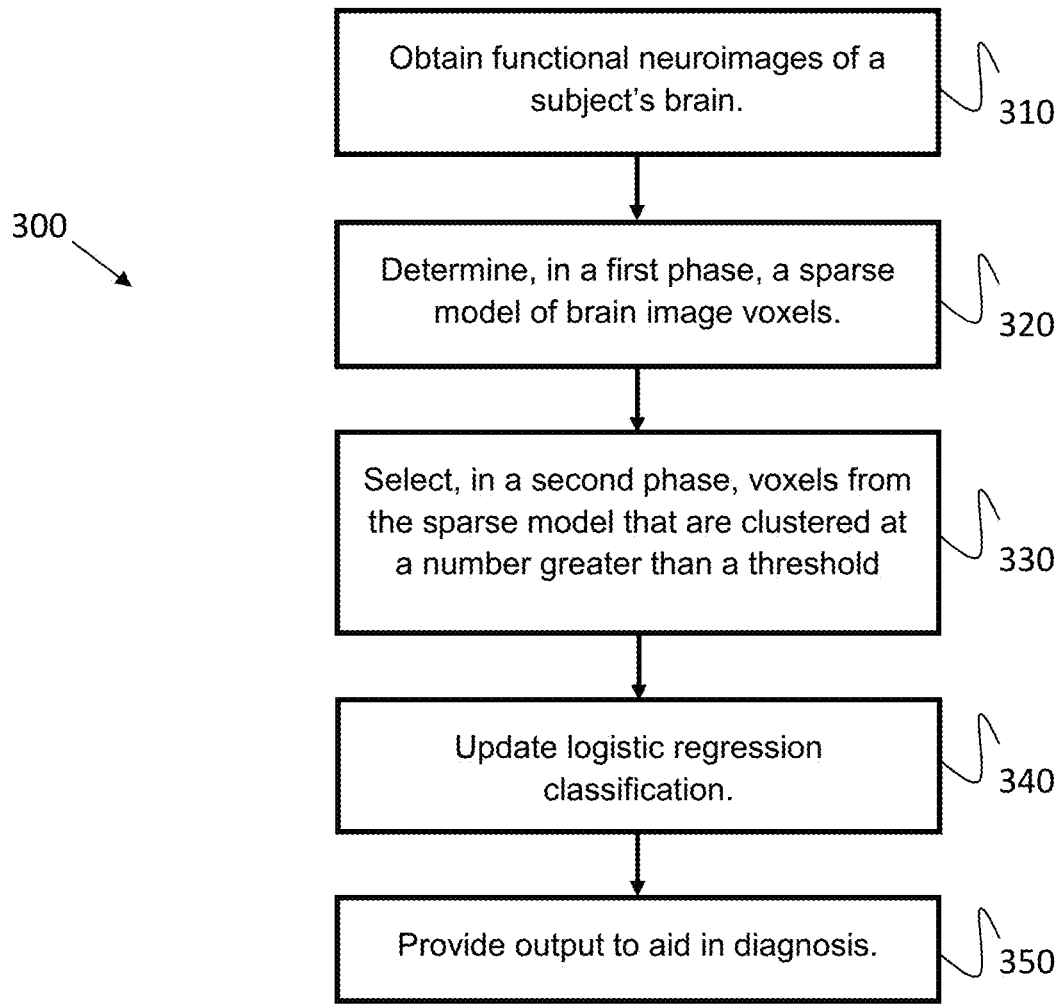
FIG. 3 illustrates a flow diagram of a dual-phase classification method to aid in diagnosis based on functional neuroimaging (fMRI) data enquired while subject(s) perform several cognitive tasks in an MRI scanner.

Certain examples employ a dual-phase classification procedure. FIG. 3 illustrates a flow diagram of a dual-phase classification method 300 to aid in diagnosis based on functional neuroimaging (fMRI) data acquired while subject(s) perform several cognitive tasks in an MRI scanner. As shown in the example of FIG. 3, at block 310, functional neuroimages (e.g., fMRI) are obtained of a subject's brain while the subject performs a series of working memory tasks. Features can be identified and dimensionality of the data reduced based on the fMRI and task data.

In a First-Phase classification, at block 320, the SLR classifier receives, for each subject, a single vector input of all voxels included in a plurality (e.g., four) of obtained fMRI images from a plurality (e.g., four) of VSWM tasks (e.g., after an initial voxel exclusion using a univariate analysis). In some examples, the SLR classifier may be uninformed about a respective spatial location of voxels, or a brain image (associated with a specific behavioral task) from which a voxel was taken. In this classification phase, sparsity is enforced using an optimization procedure that includes two runs—a first run involving a fast search for a best possible sparsity range, and a second run involved tuning and determining an optimized sparsity level.

For a Second-Phase classification, at block 330, after discovery of the optimized sparse model in the First-Phase, alternative models are tested using only those voxels that were clustered together in voxel-clusters (fROIs) with greater than a threshold number of voxels in a cluster (e.g., either more than 10 voxels in a cluster, or more than 20 voxels in a cluster, etc.). Weights are then recalculated for these voxels using the Logistic Regression classification algorithm again, this time without forcing sparsity ($\lambda=0$).

ADHD Model Discovery (First-Phase)

An objective of the First-Phase Sparse Logistic Regression (SLR) based classification and/or other LR-based classification is to detect a distributed brain network providing a brain model of ADHD. The (S)LR classifier is used for a multivariate pattern analysis at the whole brain level, being provided with multiple (e.g., four) fMRI images from multiple (e.g., four) VSWM tasks as input data (when using the SLR, each functional voxel counts as an input feature for the classifier; when using the LR, each PC counts as an input feature for the classifier).

In some examples, in an earlier feature selection phase voxels that show no sensitivity to the VSWM tasks as compared with the baseline fixation tasks can be excluded. In some of these examples, a univariate analysis is used to average together the fMRI images from the n-back tasks (e.g., 1-back, 2-back, etc.) from a plurality of experimental conditions and all participants from both the clinical group and the control/normal group. By setting a voxel selection threshold (e.g., $p<0.025$) to select voxels showing significant activation or deactivation in the VSWM tasks (compared to the fixation tasks) in large voxel clusters (e.g., clusters of 100 voxels or more), many non-relevant (e.g., 'noisy' voxels) brain voxels can be excluded from the input of the SLR classifier, which shorten the model search time and may improve accuracy of the classifier.

Next, the SLR classifier is used to detect which of the remaining voxels are most informative for discriminating between ADHD children and non-ADHD children. In certain examples, forcing sparsity results in substantial voxel/feature pruning, reducing the chance of discovering an ADHD model with good classification performance resulting primarily from inclusion of a large number of marginally informative features/voxels.

Model Tuning (Second-Phase)

An objective of the Second-Phase Logistic Regression classification is to tune the ADHD model discovered in the First-Phase. Model tuning involves selecting a more structured brain network while, ideally, preserving qualities of the ADHD model discovered in the First-Phase. For example, an ADHD brain model can be based on informative voxels that are clustered together. Such a model is less likely to be susceptible to overfitting as it is more likely that voxels with diagnostic value in spatially normalized fMRI images of different individuals will be, at least partially, mapped into the model spatial template. Accordingly, in the Second-Phase, voxels found in small clusters in the First-Phase model are excluded. After the exclusion of the smaller voxel-clusters, at block 340, a Logistic Regression classifier is used to recalculate the weights of the remaining voxels (in some examples, using a leave one subject out cross validation procedure). This allows the final model to preserve the capacity to diagnose ADHD with high precision while maintaining high tolerance to overfitting.

At block 350, an output is provided to aid in diagnosis of a behavioral issue, such as ADHD. An output model can be used by systems and methods to automatically identify and diagnose ADHD in a subject.

Certain examples classify subjects using several measurements for each subject (e.g., fMRI data from a few distinct VSWM tasks), wherein each measurement enables a better than chance classification accuracy and wherein there is a substantial degree of independence between the measurements (e.g., distinct cognitive tasks), results in higher classification accuracies compared to accuracies achieved using data from each single measurement, for example. Manifestation of neurocognitive abnormalities in ADHD is context dependent.

Figure 4:
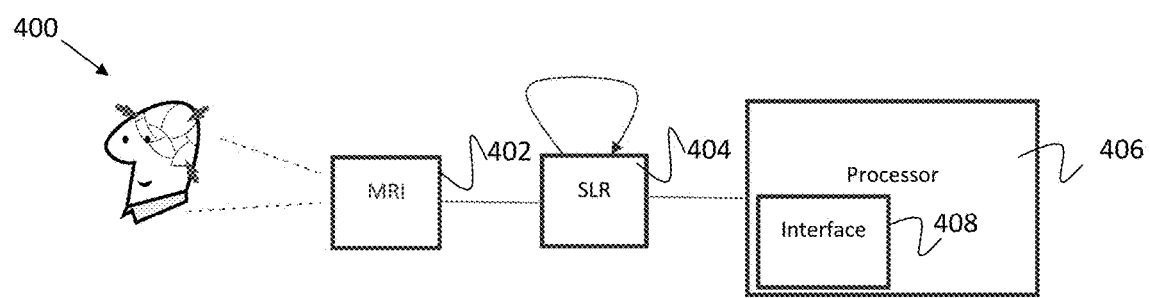
FIG. 4 illustrates an example fMRI data analysis system.

FIG. 4 illustrates an example analysis system 400 that can be used to implement methods disclosed and described herein. For example, an image scanner, such as an MRI scanner 402, can obtain one or more functional images of a patient, and the information can be fed to a classifier 404, such as logistic regression (LR) or sparse logistic regression (SLR) classifier. The classifier processes the image (e.g., voxel, cluster of voxels, etc.) data in one or more passes (e.g., a first phase, a second phase, etc.) and provides an output to a processor or processing system 406. The processor 406 includes an interface (e.g., a graphical user interface) by which to display output (and receive user input to interact with the output). An example output is shown in FIGS. 2A-2J. FIGS. 2A-2D show a collection of fMRI data and a first-phase classification of voxels from the fMRI images. FIGS. 2E-2J show a second-phase voxel cluster selection and hierarchical clustering.

Example Pattern Analysis Using a Sparse Logistic Regression Classification Algorithm As described above, in some examples, Sparse Logistic Regression (SLR) is useful for bioinformatics applications in which high dimensionality of data hinders effective feature selection, and the presence of relatively small samples makes most other classifiers susceptible to overfitting. SLR addresses both issues by adding a regularization term $l_1$ to a classic Logistic Regression model. In additional example detail, let $D=\{(x^i, y^i)|1\leq i\leq m\}$ represent the training data set, where $x^i \in R^N$ and $y^i \in \{+1, -1\}$ denote the $i^{th}$ subject's N-dimensional input vector and binary class label, respectively. SLR then finds the weight vector $w \in R^N$ by solving:

$$\operatorname*{argmin}_{w,b} \sum_{i=1}^{m} \log(1 + \exp(-y^i(w^T x^i + b))) + \lambda \|w\|_1, \quad \text{(eq. 1)}$$

where m is the total number of subjects in D, $\|w\|_1$ represents the $l_1$ norm of w, b is the bias parameter, and $\lambda>0$ is the regularization parameter. The regularization term in (eq. 1) enforces sparsity on the vector w, whose each entry can be interpreted as the contribution of its corresponding feature (voxel) in determining the final labels. In particular, voxels whose corresponding entries in w are zero can be discarded from the model, thus resolving the feature selection problem in parallel with the model optimization. The number of non-zero entries in w, or equivalently the number of selected features, is controlled by $\lambda$ whose value should be set in a trade-off between having a sparse weight vector and minimizing the logistic loss. Upon solving (eq. 1), the optimal parameters, denoted by w* and b*, are used to find the probability of a new subject (with input vector $x^{new}$) suffering from ADHD, as follows:

$$p(y^{new} = +1) = \frac{1}{1 + \exp(-w^{*T}x^{new} + b^*)}. \quad \text{(eq. 2)}$$

Since the problem in Equation 1 is convex, convergence to a global optimum is guaranteed for a fixed $\lambda$ using any convex optimization scheme. For example, a Projected Scaled Sub-gradient (PSS) algorithm can be employed. The PSS algorithm is a quasi-Newton method that builds an approximation to the Hessian of the logistic loss function. PSS has linear complexity (O(N)) both in space and time, and hence is well-suited for large-scale problems.

To select the value of the regularization parameter $\lambda$, a leave-one-out cross-validation procedure, suitable for small to mid-sample size, can be used, for example. This procedure includes two nested loops. In the outer loop, $\lambda$ is set in turn to each of the members of the pre-determined sequence $\{\lambda_j\}_{j=1}^P$. In the inner loop, for each of the m subjects (e.g., 40 boys), the selected value for $\lambda$ is used to find $w^*$ on a training set formed by excluding subject's data, which is later used as the single member of a validation set to evaluate the performance of the learned model. Upon termination of the inner loop, the average cross-validation accuracy (CVA) is computed as the performance evaluation metric, via $$CVA = \frac{1}{m}\sum_{i=1}^{m} \delta(y^i, \text{sgn}(p(y^i = +1) - .5)), \quad \text{(eq. 3)}$$

where $\delta(.,.)$ and $\text{sgn}(.)$ respectively denote the Kronecker delta and sign functions. Finally, the $\lambda$ with the highest CVA is chosen and used along with the entire data set D for learning the final model. The pseudo-code in Algorithm 1 below summarizes an example described procedure. In the First-Phase, an algorithm such as Algorithm 1 can be run twice to allow for a fine-tuning of the regularization parameter. In order to cover a wide range of values, in the first run the value of $\lambda$ is varied logarithmically, ranging between $10^{-8}$ to 1. In the second run, the value of $\lambda$ is varied linearly around the best $\lambda$ found in the first run.

---
Algorithm 1.
---

For all $\lambda \in \{\lambda_j\}_{j=1}^P$
  $\lambda \leftarrow \lambda_j$
  For all subjects $1 \leq i \leq m$ in the set D
    Solve (eq.1) on the set D excluding the $i^{th}$ subject $(x^i, y^i)$
    Use the optimal parameters found above in (eq.2) to predict $y^i$
  End For
  Evaluate the average cross-validation accuracy for $\lambda_j$ as in (eq.3)
End For
Choose $\lambda \in \{\lambda_j\}_{j=1}^P$ associated with the highest cross-validation accuracy
Solve (eq.1) on the entire set D and learn final $w^*$.

---

For each subject, the SLR classifier receives as input a single vector of all the voxels included in plurality of fMRI images from the plurality of VSWM tasks (e.g., after an initial voxel exclusion). The SLR classifier is uninformed about the respective spatial location of voxels, or the fMRI image from which a voxel was taken.

In the Second-Phase, after the discovery of a sparse model in the First-Phase, voxels clustered in large clusters (e.g., either K≥10 or K≥20 voxel-clusters) are selected. Weights are then recalculated for these voxels using the Logistic Regression classifier without enforcing sparsity ($\lambda$=0).

Thus, a Sparse Logistic Regression (SLR) classifier enables discovering a model allowing reliable ADHD diagnosis based on neuroimaging data acquired while participants perform a plurality of behavioral tasks (e.g., four distinct visuospatial working memory (VSWM) tasks).

Example Systems and Methods for ADHD Classification Modeling and Prediction

Certain examples provide a plurality of advantages over other neuroimaging based diagnosis procedures including: (i) Acquiring functional neuroimaging data while participants perform an ensemble of distinct cognitive tasks, targeting several cognitive functions impaired in the clinical population, increases the chance that distributed abnormal patterns of neural activity characterizing the clinical population will be detected and more easily differentiated from irrelevant individual differences (such as age, gender, or generic cognitive skills); (ii) The use of a classification algorithm that learns a model that is based only on the most informative voxels in the brain, while discarding information from other voxels, allows capturing the core differences between the clinical group and the normal population (balancing between inclusion of sufficient number of voxels, but a small enough brain volume to reduce susceptibility to confounding factors).

Major brain-networks taking part in the discovered ADHD model include the visuospatial working-memory, attention, reward-processing and error-monitoring brain networks, all of which are directly associated with the cognitive tasks performed by the participants. Because altered patterns of neural activity in ADHD depend on the performed cognitive task, the SLR classifier benefits from being provided with fMRI data acquired from a few distinct tasks. In order to further investigate the nature of differences between the ADHD and NC boys in the different VSWM tasks, a descriptive univariate analysis can be conducted (e.g., using an uncorrected voxel selection threshold of p<0.005, in clusters with 10 voxels or more). A high correspondence can be found between voxels showing differences in mean level of neural activity between the ADHD and NC groups and the voxels taking part in the K≥10 SLR classifier ADHD model, for example.

Referring to overlaps with voxel-clusters in the example K≥10 cluster ADHD model, a univariate analysis shows that, in the large-reward no-feedback condition, NC boys exhibit higher levels of neural activity (compared with ADHD boys) in the left and right middle frontal gyrus (MFG), brain regions playing an executive role in the VSWM network. NC boys also exhibit higher activity in the left and right precuneus, brain regions associated with visuospatial processing. Boys with ADHD, on the other hand, exhibit higher activity in the left inferior parietal lobe (IPL), a brain region associated with sensory aspects of working memory, predominantly in verbal tasks, and in the left middle and superior temporal gyrus (MTG/STG), brain regions associated with verbal processing, but also associated with the ventral, bottom-up, attention network. In the large-reward with-feedback condition, voxel-clusters with significant contribution to the SLR classifier are evident in the left fusiform gyrus, implicated in letter processing, where ADHD boys exhibited higher activity. This is in contrast to a voxel-cluster in the left angular gyrus, implicated in visuospatial processing, where NC boys exhibited higher activity. These results suggest that boys with ADHD have lower capacity, compared with NC boys, in suppressing task-irrelevant information (e.g., a letter identity instead of its spatial location).

In the small-reward without feedback condition, the SLR classifier made use of smaller voxel-clusters in the superior parietal lobules (SPL) and in prefrontal cortices (SFG, IFG, MeFG, Insula), all associated with attention, working memory and cognitive control. In all of these brain regions, NC boys exhibited higher neural activity compared with ADHD boys. Finally, in the small-reward with-feedback condition ADHD boys exhibited higher activity in the ventral-frontal/orbitofrontal cortex. This brain region is primarily involved in reward processing, but it is also associated with the ventral, bottom-up attention network. Higher degree of orbitofrontal deactivation is associated with greater capacity to discard distracting stimuli. This again indicates poor capacity of ADHD boys in suppressing task-irrelevant information, such as feedback associated with small-reward.

Due to the good fit of the model (e.g., high classification accuracy and low probability of being overfitted), high classification accuracies can be obtained if testing the ADHD model on fMRI images acquired after rescanning the same participants in somewhat different conditions, or even if testing the SLR classifier on less typical NC and ADHD cases.

In certain examples, the SLR classifier capacity to discover a useful ADHD model depends on an effective manipulation of the cognitive/behavioral tasks.

The ADHD diagnosis accuracies show that functional neuroimaging can be used as an applicable tool for diagnosing neurological and psychiatric disorders. In certain examples, the presently disclosed data analysis procedure also provides an important methodological contribution showing how pattern analysis can be implemented in diagnosis procedures, by accounting for the possibility of model overfitting and diagnosis biases due to confounds. Similar methodologies can be applied for diagnosing other neural and psychiatric disorders for which there is no available reliable objective diagnostic procedure.

Using an LR classifier that receives brain imaging data (fMRI) input acquired while subjects perform four distinct VSWM tasks enable a high accuracy of ADHD classification (e.g., 92.5%). In certain examples, manifestation of neurocognitive abnormalities in ADHD is context dependent. For example, in an absence of trial-by-trial feedback, altered activity patterns characterizing ADHD are most evident in the brain's bilateral middle frontal gyri (MFG), specially the right MFG. The MFG plays an executive role in the visuospatial working memory network and a primary role in volitional (top-down) allocation of attention. In VSWM tasks without feedback, subjects with ADHD exhibit lower levels of activity in the MFG when compared to TD subjects.

In other examples, fMRI data from small-reward with feedback VSWM tasks contributes to ADHD classification by identifying altered brain activity primarily in the brain's bilateral orbitofrontal cortex (bi-OFC) and left fusiform gyms (left-FFG). The OFC is involved in monitoring which actions are rewarded and predicting which future actions are likely to be rewarded. The left-FFG is involved in letter identification and reading. TD subject exhibit greater deactivation in these two brain regions when compared to ADHD subjects, primarily in the small-reward with feedback VSWM task. ADHD subjects may fail in suppressing task irrelevant information (e.g., letter identity in a task that involves monitoring spatial location of letters and visual feedback indicating an insignificant reward, etc.).

In some examples, features with significant loadings on a small-reward with feedback VSWM task are two fROIs in the right medial/superior prefrontal gyrus (right-MeFG- and right-MeFG+), left-MFG, right superior temporal gyrus (right-STG), right anterior insula (right-AntIns), and right supramarginal. These brain regions are involved in feedback processing, bottom-up attention, and sensory integration. In the small-reward with feedback condition, subjects with ADHD are likely to exhibit altered suppression of irrelevant visual features (FFG), altered visuospatial processing (precuneus), altered sensory integration (STG and supramarginal), altered bottom-up attention control (OFC), altered feedback processing and top-down attention control (MeFG and MFG), and altered synchronization between bottom-up and top-down attention control (AntIns), for example.

In some examples, fROIs in the right-AntIns and right-MeFG in or large or small reward with feedback VSWM task are associated with altered feedback processing in ADHD (regardless of reward expectation). These regions (together with the anterior cingulate) mediate between a central executive network and brain regions involved in risk/gain prediction where response selection is required. In some examples, subjects with ADHD may exhibit poor cognitive control associated with lower levels of neural activity in the anterior insula compared with TD subjects.

Thus, using fMRI data from a plurality (e.g., four) of distinct VSWM tasks enables improved classification accuracies over use of fMRI data from a single VSWM task. In some examples, a number and/or duration of cognitive tasks may vary to implement a diagnosis tool for ADHD. In some examples, multi-task-based fMRI can be integrated with resting-state fMRI and structural imaging to enable an effective diagnosis of most clinical cases, as well as detection of onset of some clinical condition in early childhood. Tools using fMRI data provide better classification accuracies than corresponding behavioral data such that even ADHD cases exhibiting normal-like VSWM performance can be characterized by an altered pattern of brain activation.

Certain examples focus on clusters of voxels representing brain activity in regions of interest based on task execution during imaging (fROIs). Rather than a two phase sparse model analysis, certain examples develop an ADHD classification model and then apply it to aid in ADHD diagnosis of a patient or other subject. In certain examples, the classification model can be refined based on data from application to subject(s).

Figure 5:
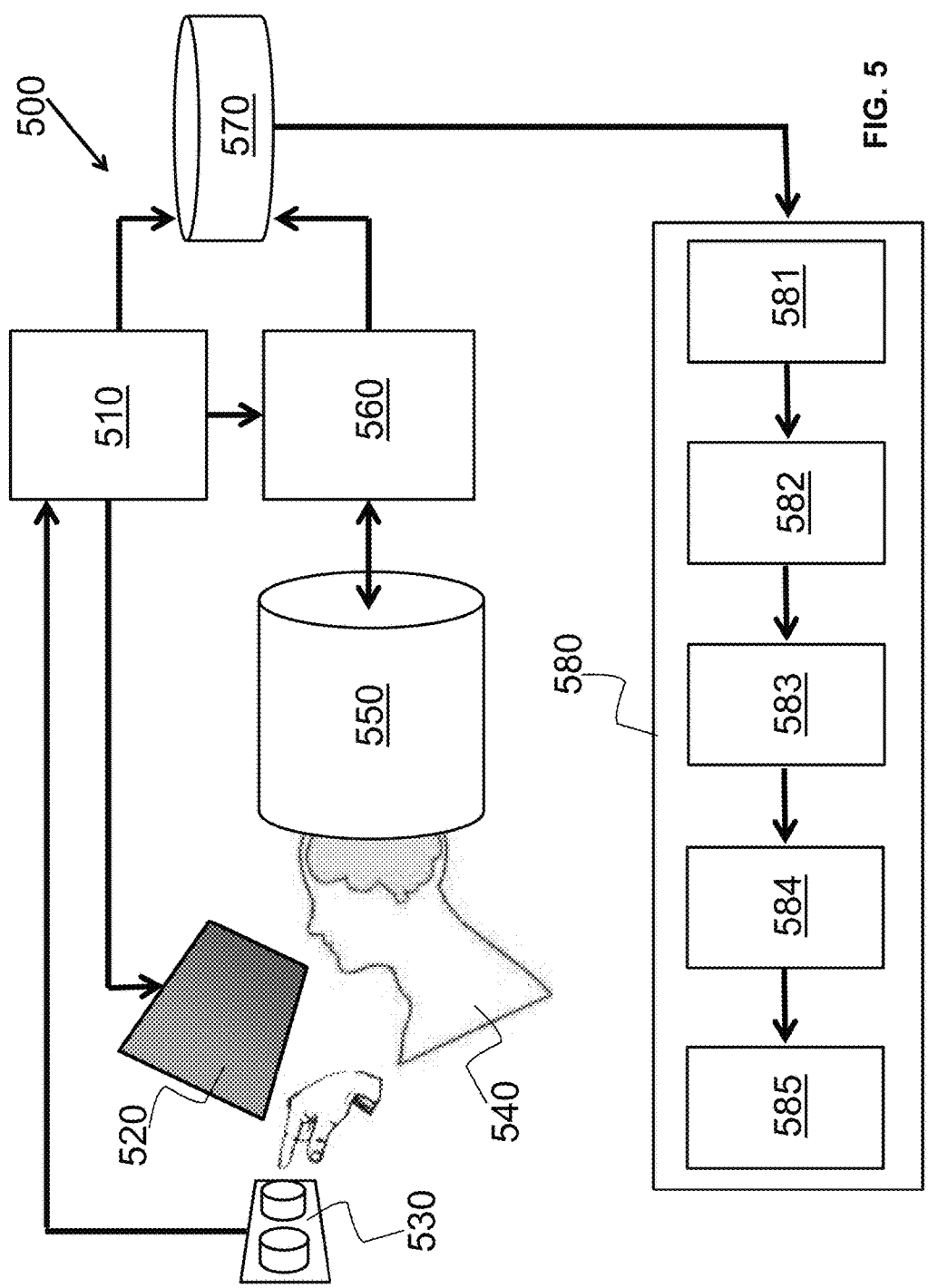
FIG. 5 illustrates an example system to generate an ADHD model based on an 'algorithm training sample' from acquisition of brain activity of a verified ADHD and normal subjects.

FIG. 5 illustrates an example system 500 to generate an ADHD model based on an 'algorithm training sample' from acquisition of brain activity of a verified ADHD and normal subjects.

As shown in the example of FIG. 5, to acquire brain activity data, a first computer 510 displays stimuli of four distinct Visuospatial Working Memory (VSWM) tasks on a computer display 520 mounted in an MRI scanner 550. A subject being scanned 540 performs the VSWM tasks by pressing keys on a response box 530. The subject's responses are recorded by the same first computer 510 used to run the VSWM tasks. The first computer 510 is also used to trigger a second computer 560 that controls the MRI scanner 550. The first computer 510 triggers the second computer 560 at the beginning of each scan, for example, to help ensure that the two computers 510, 560 are synchronized. Behavioral data from the first computer 510 and brain imaging data from the second computer 560 are stored on a data storage device 570.

A third computer 580 uses the brain imaging data and the behavioral data acquired from a sample of typically developed subjects and ADHD subjects (e.g., subjects with confirmed diagnosis) to learn a brain activation model of ADHD. A first processing stage 581 of the third computer 580 is a preprocessing stage to preprocess the brain imaging and behavioral data. For example, preprocessing such as adjustment of slice timing, realignment of functional images, co-registration of functional and anatomical images, normalizing of images to a template image, movement reduction, etc., can be performed on acquired brain image data.

A second processing stage 582 of the third computer 580 involves identifying and extracting brain activation from brain regions which are most likely to be involved in VSWM tasks in a broad population. Identifying and extracting brain activation information involves use of the functional brain imaging data of the entire sample, from all four VSWM tasks, to detect functional Brain Regions of Interest (fROIs). For example, a univariate GLM analysis can be used to select features based on an identification of functional brain regions of interest (fROIs) that show significant activation or deactivation in all four VSWM tasks contrasted with fixation tasks.

In a third processing stage 583, the brain imaging data from the 16 fROIs discovered in the second processing stage 582 is extracted, separately from each subject, for each of the four VSWM tasks. The extraction results in, for example, a total of 64 features describing a pattern of brain activation of each individual subject. The third processing stage 583 is followed by a dimensionality reduction of the data in a fourth processing stage 584, such as using a Sparse Principle Components Analysis (SPCA). Using SPCA, the brain imaging data of each subject can be reduced to a relatively small number (e.g., 10) orthogonal principle components (PCs), where each PC is recalculated based only on a few features with highest loadings, for example.

A fifth processing stage 585 includes a supervised Logistic Regression (LR) classifier to learn which PCs best differentiate between the typical development (TD) cases and the ADHD cases. For example, the LR classifier is fed the 10 PCs as input variables to determine an accuracy, sensitivity (e.g., correct classification of ADHD in subjects), and specificity (e.g., correct classification of typical development subjects). SPCA can be used to reduce a number of variables fed to the classifier, and PCs can be recalculated based on features with highest loadings so as to exclude lower weight features that are likely to mostly add noise. Each resulting PC may be affected by relatively few features, where each feature affects at most one PC, enables better determination of underlying neurocognitive mechanisms represented by each PC, for example. Sparse loadings selection can be facilitated based on a thresholding of rotated loadings, for example.

Figure 6:
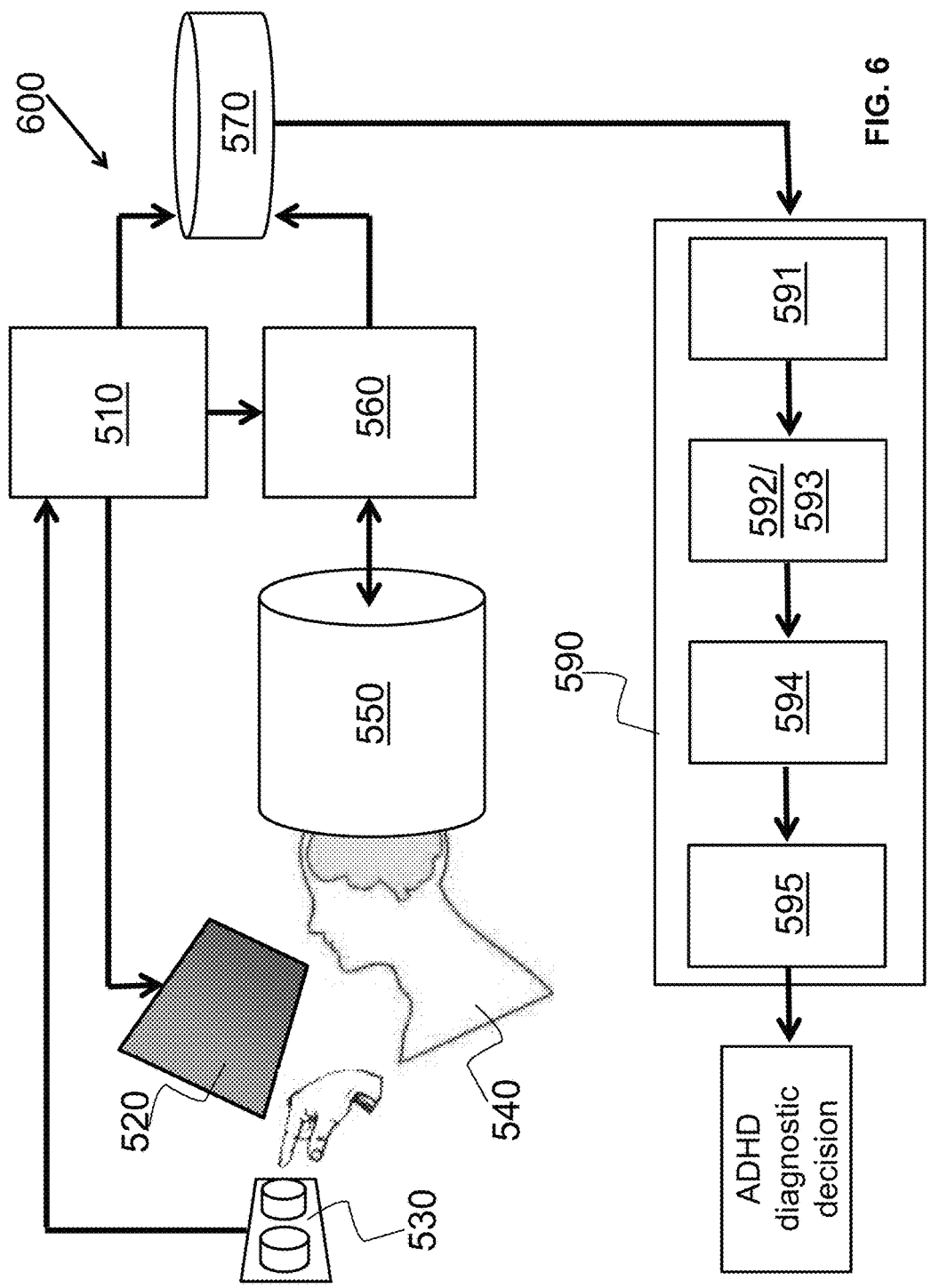
FIG. 6 illustrates an example system configured to use an earlier learned ADHD model to diagnose new cases of ADHD.

FIG. 6 illustrates an example system 600 configured to use an earlier learned ADHD model to diagnose new cases of ADHD. As described above with respect to the example of FIG. 5, to acquire brain activity data, the system 500 includes the first computer 510 which displays stimuli of four distinct Visuospatial Working Memory (VSWM) tasks on the computer display 520 mounted in the MRI scanner 550. The subject being scanned 540 performs the VSWM tasks by pressing keys on the response box 530. The subject's responses are recorded by the same first computer 510 used to run the VSWM tasks. The first computer 510 is also used to trigger the second computer 560 that controls the MRI scanner 550. The first computer 510 triggers the second computer 560 at the beginning of each scan, for example, to help ensure that the two computers 510, 560 are synchronized. Behavioral data from the first computer 510 and brain imaging data from the second computer 560 are stored on the data storage device 570).

A third computer 590 uses the brain imaging data and the behavioral data that was acquired from a subject to diagnose new cases. A first processing stage 591 of the computer 590 is a preprocessing stage of the data (e.g., substantially similar or identical to first processing stage 581 of the second computer 580). A second processing stage 592/593 involves extraction of brain activation from the same fROIs discovered in the second processing stage 582 of the second computer 580. The second processing stage 592/593 of the third computer 590 is followed by a dimensionality reduction of the data in a fourth processing stage 594 into principle components and parameters calculated based on the subject sample used in the model discovery stage (e.g., by the second computer 580. A fifth processing stage 595 is based on a Logistic Regression (LR) classifier that uses the model discovered in the fifth processing stage of the second computer 585 to generate an ADHD diagnostic decision (e.g., determine if the new subject has ADHD).

Figure 7:
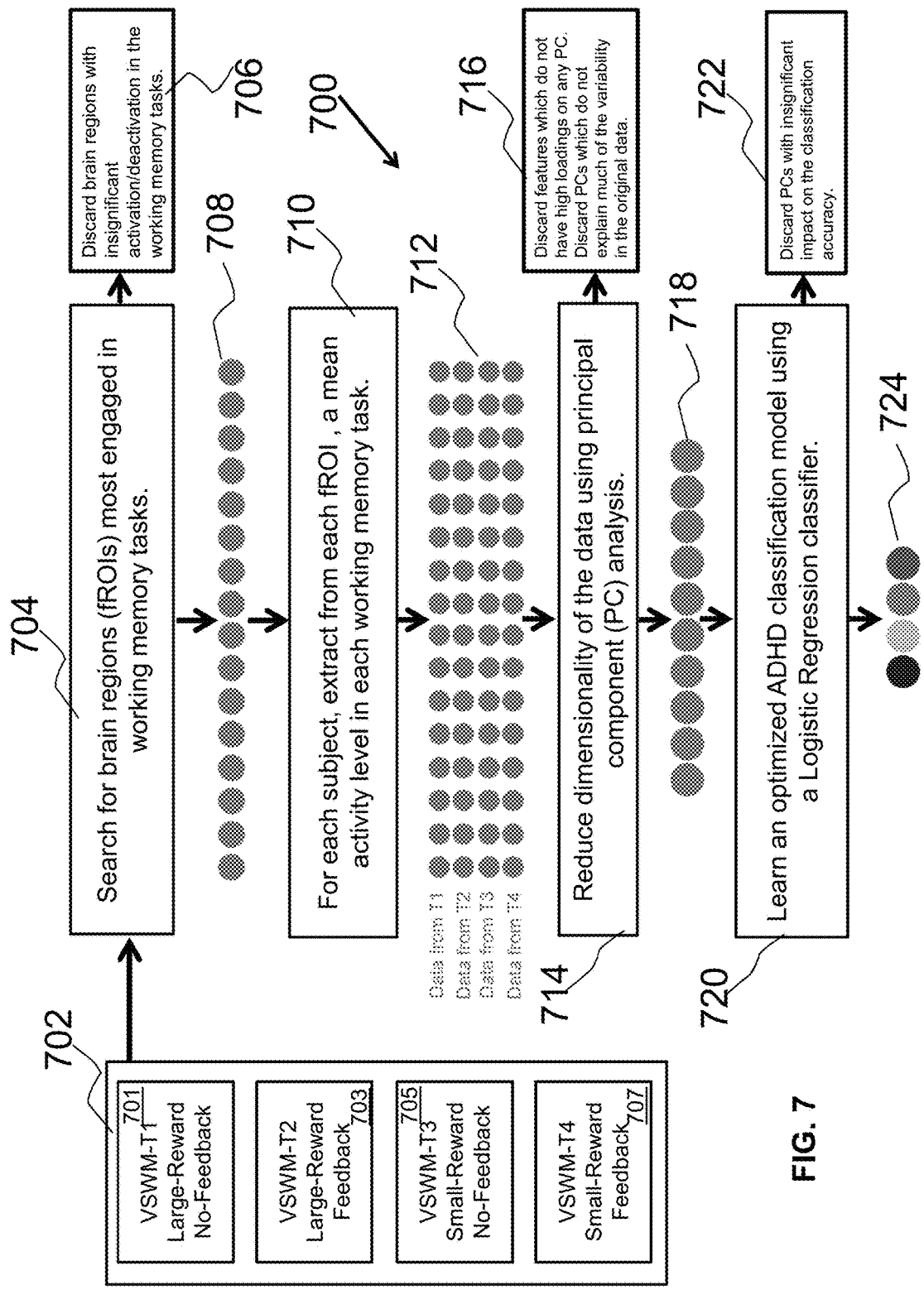
FIG. 7 illustrates a flow diagram of an example method to determine an ADHD model based on a verified ADHD subject sample and a normal subject sample.

FIG. 7 illustrates a flow diagram of an example method 700 to determine an ADHD model based on a verified ADHD subject sample and a normal subject sample. At block 702, functional brain images are input for each subject. The functional brain images (e.g., fMRI) can be obtained while the subject is performing a series of tasks (e.g., four VSWM tasks for each subject, etc.). For example, a first VSWM task 701 involves a large reward and no feedback; a second VSWM task 703 involves a large reward and feedback to the subject, a third VSWM task 705 involves a small reward and no feedback, and a fourth VSWM task 707 involves a small reward and feedback to the subject.

The input fMRI images from VSWM tasks is provided and, at block 704, brain regions (fROIs) that are most engaged in working memory tasks are identified. For example, using data from all subjects and all tasks, fMRI data is correlated against VSWM tasks to identify which fROIs exhibited significant activation or deactivation in comparison to fixation tasks (e.g., VSWM>Fix or Fix>VSWM).

Figure 9A:
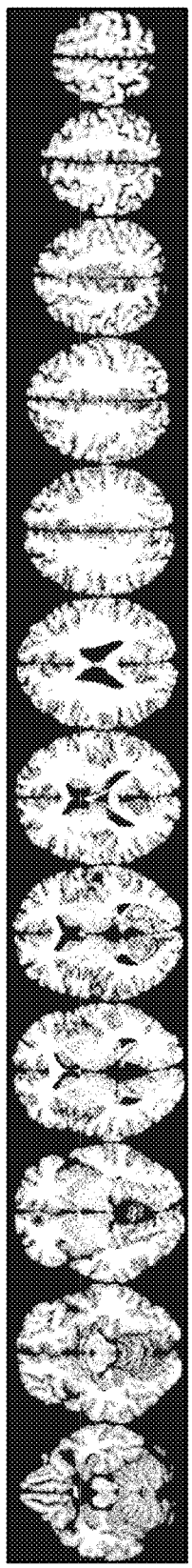
FIGS. 9A-9C illustrate example neuroimaging data showing activation or deactivation indicating potential regions of interest contrasted between the working memory tasks and a control fixation task to form task-related activity profiles.
Figure 9B:
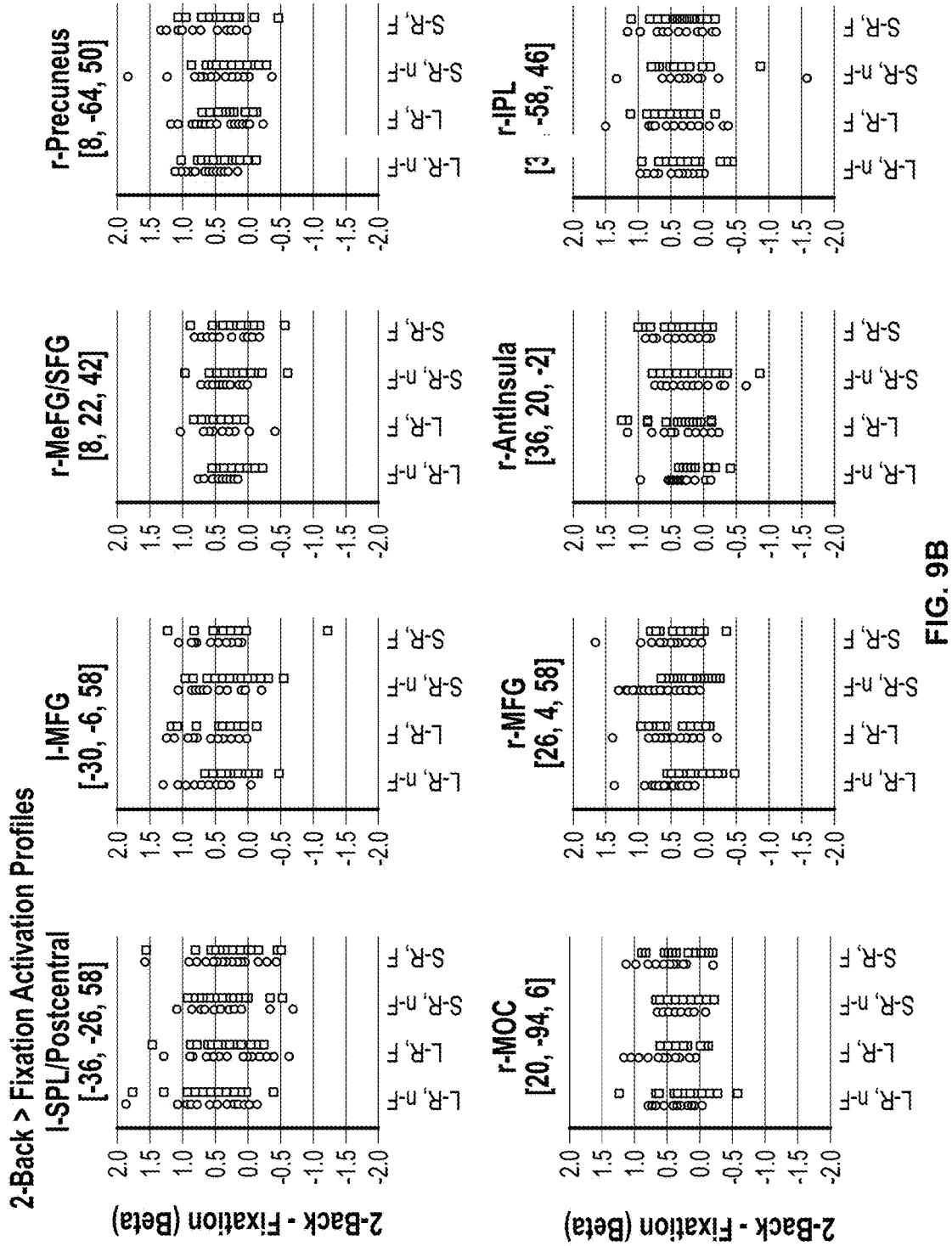
Figure 9C:
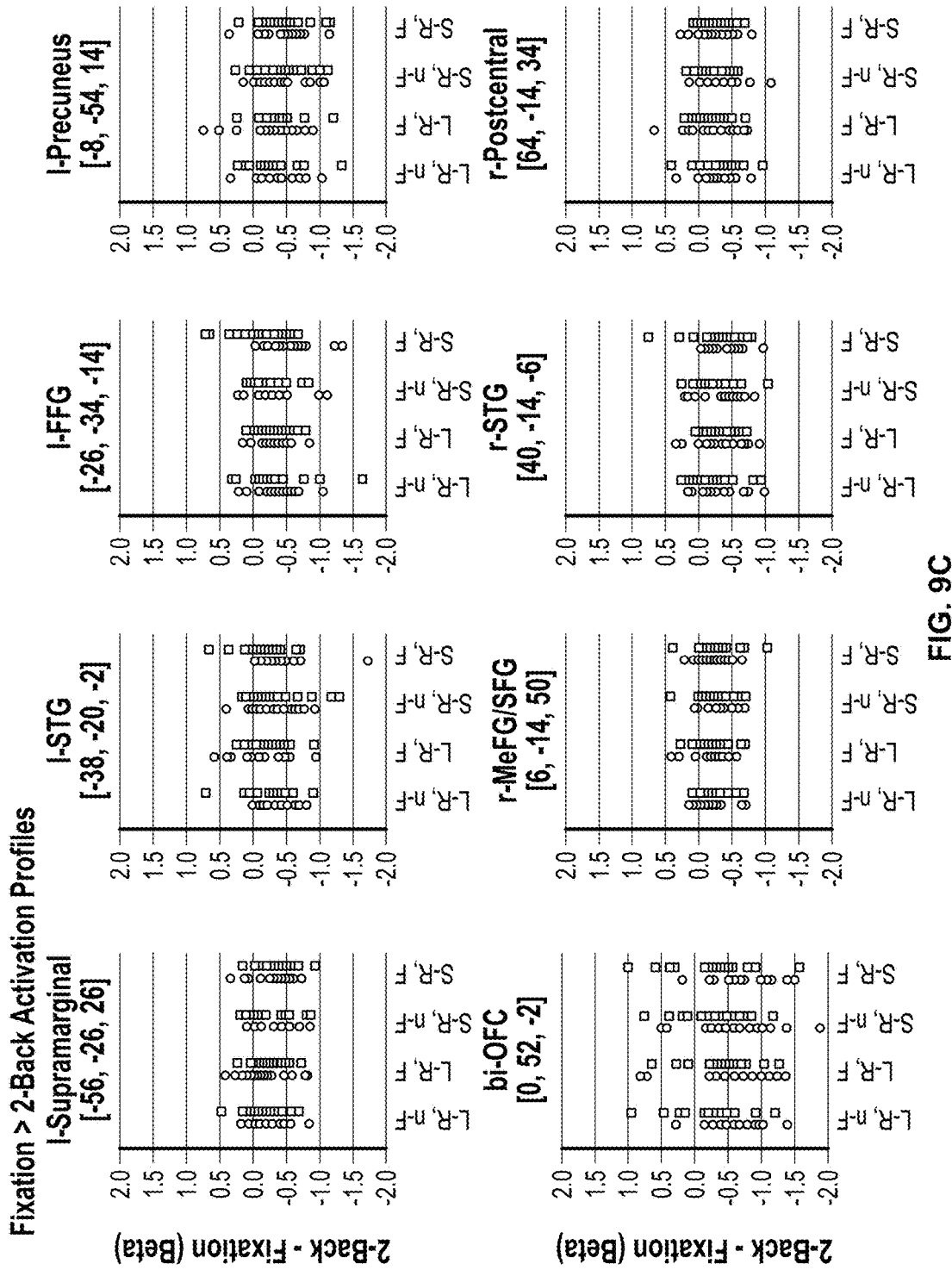

As depicted in an example in FIGS. 9A-9C, fMRI data showing activation or deactivation indicating potential fROIs (e.g., each region is a cluster of at least 50 voxels with similar activation profile) can be contrasted between VSWM tasks and fixation tasks to form activity profiles in activated and deactivated fROIs among participants in VSWM tasks. In the example of FIG. 9A, activated regions (fROIs) are contrasted (e.g., in orange) with deactivated regions (e.g., in purple) in VSWM tasks contrasted with fixation tasks. FIGS. 9A and 9B illustrate example activity profiles in activated fROIs and deactivated fROIs, respectively. Each data point represents a single participant in a single VSWM task (e.g., red represents ADHD cases and blue represents TD cases). As shown in the examples of FIGS. 9B and 9C, "standard" brain coordinates from the Montreal Neurological Institute (MNI coordinates) for each fROI are shown in brackets (ordered from left-most to right-most), in conjunction with the following notations: L-R indicates a large-reward task, S-R indicates a small-reward task, n-F indicates no-feedback, and F indicates feedback. In FIG. 9B, brain regions showing activated fROIs include left Superior Parietal Lobe (l-SPL), left Middle Frontal Gyms (l-MFG), right Medial/Superior Frontal Gyrus (r-MeFG/SFG), right Middle Occipital Cortex (r-MOC), right Anterior Insula (r-AntInsula), and right Superior Parietal Lobe (r-IPL). In section (C)

of FIG. 9C, brain regions showing deactivated fROIs include left Superior Temporal Gyrus (l-STG), left Fusiform Gyrus (l-FFG), bilateral (medial) Orbitofrontal Cortex (bi-OFC).

At block 706, brain regions with insignificant (e.g., not meeting both criteria of p<0.01 Family Wise Error corrected voxel-level significance and p<0.01 Family Wise Error corrected cluster-level significance, with at least 50 voxels clustered together, etc.) activation/deactivation in the VSWM tasks are discarded. At block 708, brain regions (e.g., 16 fROIs) found to be significantly activated or deactivated (see criteria above) in all VSWM tasks are provided for further analysis.

At block 710, for each subject, a mean activity across all voxels (e.g., in units of Beta value, which is a common measure of blood oxygen level calculated from the functional brain images, etc.) is extracted from each fROI (e.g., 16 fROIs identified at blocks 704 and 708) for each VSWM task (e.g., 4 VSWM tasks) and forms a feature characterizing the brain activation of each subject (e.g., with 4 VSWM tasks a total of 64 features are characterized for each subject).

At block 712, the features characterizing the brain activation of each subject (e.g., 64 features based on data from task T1, task T2, task T3, and task T4 of the 4 VSWM tasks) are provided.

At block 714, dimensionality of the data associated with the features is reduced. For example, SPCA can be used to reduce the dimensionality of the data using the data of all participants/subjects (e.g., used for the learning of the ADHD model) in a batch. For example, brain activity data for each subject can be reduced to be represented by 10 PCs based on eigenvalues associated with fROI brain regions (e.g., eigenvalue>2).

Figure 10:
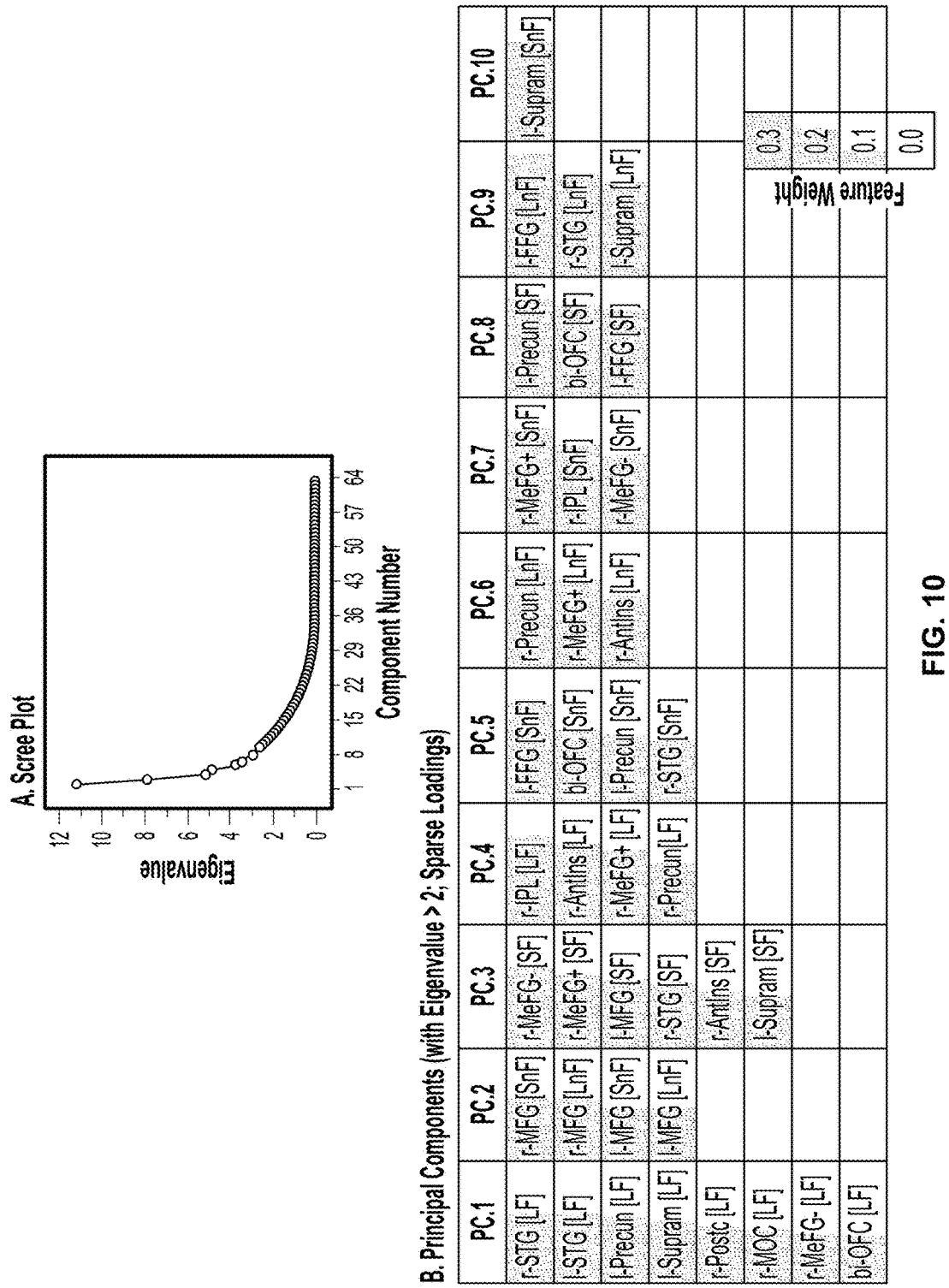
FIG. 10 illustrates an example principal component analysis outcome.

Principle component eigenvalues and sparse loadings can be determined for VSWM for tasks involving large-reward with no-feedback, large-reward with feedback, small-reward with no-feedback, and small-reward with feedback, for example, involving activated and deactivated fROIs, for example. For example, FIG. 10 illustrates an example PCA including a Scree plot of PCA eigenvalues by component number in section (A) and a sparse loading of a first 10 PCs in section (B). As illustrated in the example of section (B), experimental conditions are listed in brackets for the ten principal components with eigenvalues greater than 2, spare loadings. Experimental conditions in the example include large-reward with no feedback (LnF), large reward with feedback (LF), small reward with no feedback (SnF), and small reward with feedback (SF).

At block 716, features that do not have high loadings on any PC calculated in the SPCA (e.g., the 10 PCs) can be discarded. Additionally, PCs that do not explain much of the variability in the original data can be discarded. At block 718, the reduced PCs (e.g., 10 principal components having eigenvalues greater than 2) which together explain most of the variance in the total number of features (e.g., 64 features) are provided.

At block 720, an optimized ADHD classification model is developed using a Logistic Regression classifier. For example, a classification model can be developed by applying an LR classifier to PCs found to have significant contribution to classification accuracy (e.g., significant at p<0.05). PC significance can be determined using bootstrapping (estimating the significance of each PC based on random data sampling with replacements). The LR classifier aims finding a model so that the predicted probability (PP) of most ADHD cases is close to PP=1, and for most normal cases PP=0.

In certain examples, using cross-validation, a PC's significance can be determined. Each PC can be weighted to impact its role in determining a classification model based on a predicted probability of ADHD classification accuracy. The predicted probability can have one or more ranges or classifier decision boundary (e.g., PP=0.5; 0.33>PP or PP>0.67, etc.) with varying degrees of confidence.

For example, FIG. 11 provides an example of ADHD classification accuracies as a predicted probability (PP) of a subject being an ADHD case. Labels (e.g., color labels, patterned labels, etc.) represent a clinician diagnosis. In the example, a classifier decision boundary is at PP=0.5. A range of 0.33<PP<0.67 represents an 'ambiguity zone' in which classification decisions are made with lower confidence. PP<0.33 represents a range in which the classifier identifies with high confidence a normal case. PP>0.67 represents a range in which the classifier identifies with high confidence an ADHD case. As shown in the example of section (A) in FIG. 11, classification is based on a first ten PCs (e.g., entering 10 PCs into a regression model). As shown in the example of section (B) in FIG. 11, classification is based on four PCs found to be significant based on a leave-on-out cross validation. Section (B) also depicts respective weights (e.g., B coefficient) of each PC in the ADHD classification model.

At block 722, PCs with insignificant impact on classification accuracy are discarded. PCs with insignificant contribution to the ADHD model are defined as PCs that if excluded, the classification accuracy of a model that is based on the remaining PCs is not substantially negatively affected.

At block 724, PCs (e.g., 4 PCs) determined to have significant contribution for classification accuracies are provided in a classification model (e.g., an ADHD classification model). This classification model learning involves assigning distinct weights to each of the significant PCs (illustrated as different shades of gray). PCs with greater contribution (assigned with higher weights) to the classification accuracies in this model learning phase would have more impact on the diagnosis decision of new cases (that is, the brain imaging data from the brain regions comprising the PC is a stronger marker of ADHD, whereas PCs with lower weights are secondary indicators).

Figure 8:
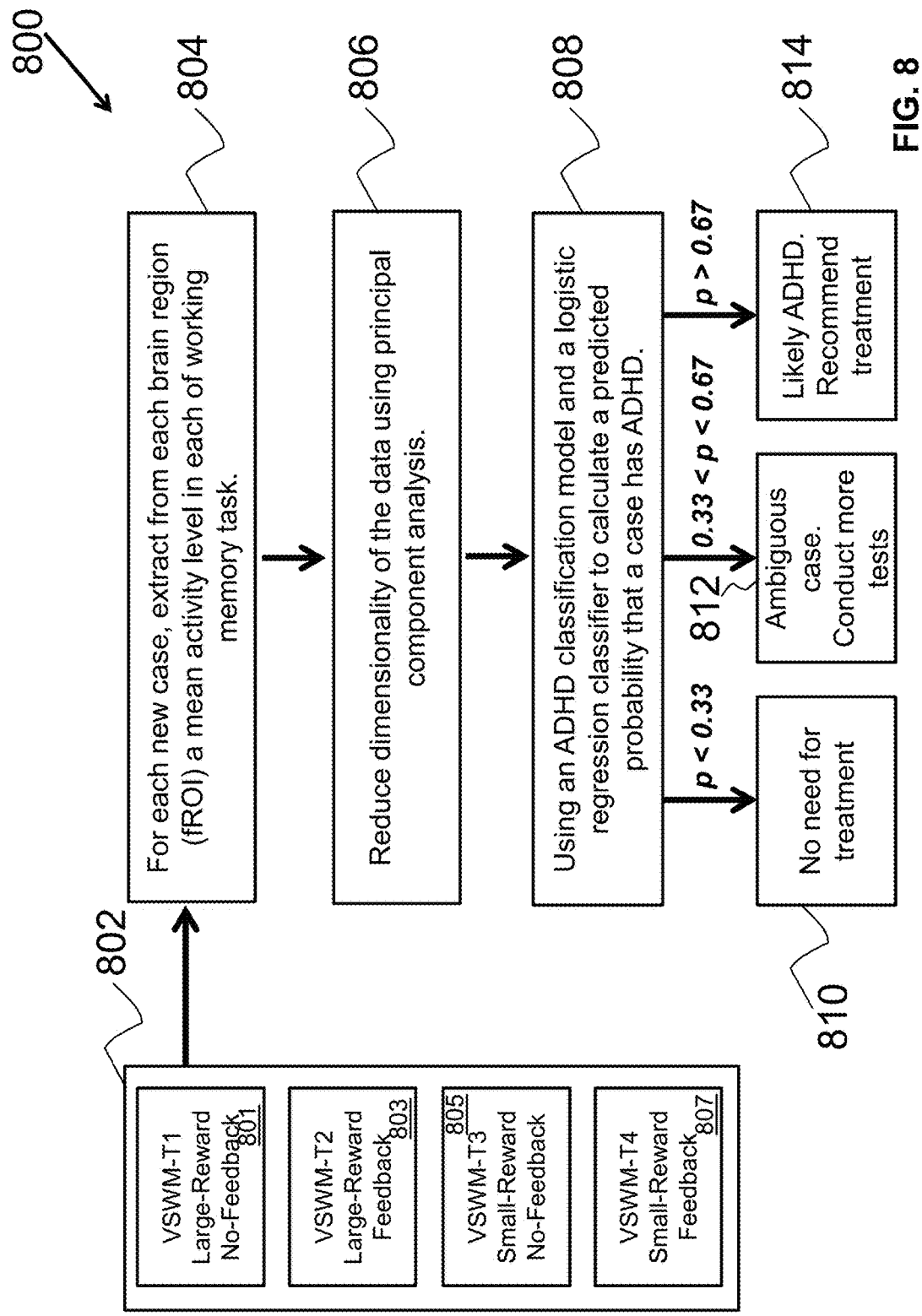
FIG. 8 illustrates a flow diagram of an example method to facilitate ADHD diagnosis using an ADHD model.

FIG. 8 illustrates a flow diagram of an example method 800 to facilitate ADHD diagnosis using an ADHD model. At block 802, functional brain images of a new test case are used as input. The functional brain images (e.g., fMRI) can be obtained while the subject is performing a series of tasks (e.g., four VSWM tasks for each subject, etc.). For example, a first VSWM task 801 involves a large reward and no feedback; a second VSWM task 803 involves a large reward and feedback to the subject, a third VSWM task 805 involves a small reward and no feedback, and a fourth VSWM task 807 involves a small reward and feedback to the subject.

The input from fMRI images from VSWM tasks is provided and, at block 804, for each subject, a mean activity is extracted from each brain region (fROI) (e.g., 16 fROIs based on an algorithm training sample such as a training sample generated according to the method 700) for each VSWM task (e.g., 4 VSWM tasks) and forms a feature characterizing the brain activation of each subject (e.g., with 4 VSWM tasks a total of 64 features are characterized for each subject). For example, mean activity can represent the mean Beta value (which is a common measure of blood oxygen level) calculated for all voxels in each brain region.

At block 806, dimensionality of the data associated with the mean activity levels is reduced. For example, SPCA can be used to reduce the dimensionality of the data using the parameters calculated based on a training sample (e.g., such as a training sample used for the method 1000). For example, brain activity data for each subject can be reduced to be represented by 10 PCs with eigenvalue>2, using the same statistics (mean and deviation from the mean) calculated for the training sample.

At block 808, using an ADHD classification model (e.g., weighted PCs such as the classification model developed using the method 1000), and a logistic regression classifier, a predicted probability that a new case has ADHD is calculated. For example, a processing system applies an ADHD classification model and LR classifier to the reduced principal component data (e.g., four significant weighted PCs) to calculate a predicted probability of ADHD. A predicted probability and associated confidence in classification accuracy can be applied to generate a classification determination, for example.

At blocks 810-814, the calculated predicted probability (PP) determines a next action by the system with respect to a new case or subject. For example, based on the classification model, predicted probability, and confidence, a determination of typical development (e.g., no need for treatment), further testing warranted (e.g., ambiguous evaluation), ADHD likely (e.g., treatment recommended), etc., can be determined and output for display, use by a clinical system, storage, etc.

For example, at block 810, if the calculated PP value is less than a first threshold (e.g., PP<0.33), then no treatment is currently warranted. At block 812, if the calculated PP value is between the first threshold and a second threshold (e.g., 0.33<PP<0.67), then results are ambiguous and more tests are ordered. At block 814, if the calculated PP value is greater than the second threshold (e.g., PP>0.67), then treatment for ADHD is recommended.

Example Processor Platform

Figure 12:
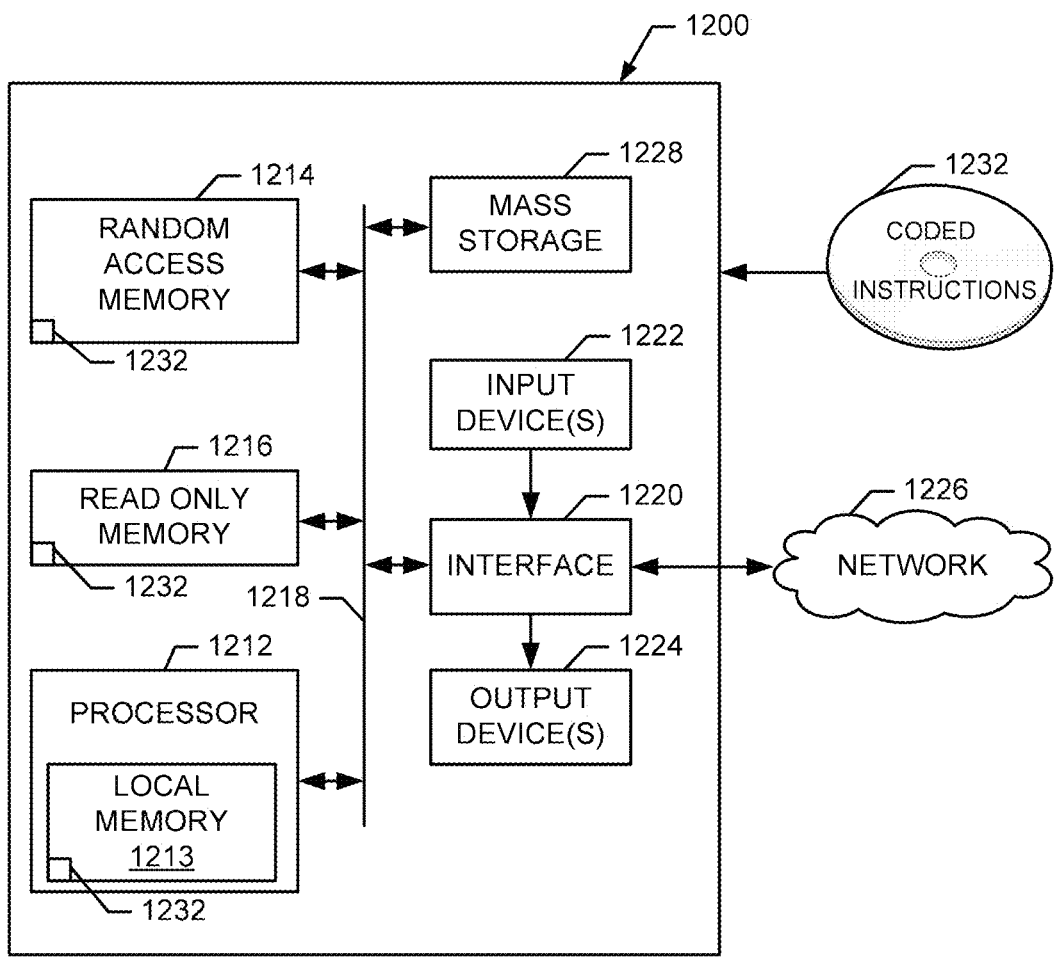
FIG. 12 is a block diagram of an example processor platform capable of executing machine readable instructions to implement systems and methods described herein.

FIG. 12 is a block diagram of an example processor platform that may be used to execute systems, methods and apparatus described herein. The processor platform 1200 is particularly configured to become a specific, specialized machine to execute and implement the example systems and methods disclosed herein. The processor platform 1200 of the instant example includes a processor 1212. For example, the processor 1212 can be implemented by one or more microprocessors or controllers from any desired family or manufacturer. The processor 1212 includes a local memory 1213 (e.g., a cache) and is in communication with a main memory including a volatile memory 1214 and a non-volatile memory 1216 via a bus 1218. The volatile memory 1214 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1216 may be implemented by flash memory and/or any other desired type of memory device. Access to the main memory 1214, 1216 is controlled by a memory controller.

The processor platform 1200 also includes an interface circuit 1220. The interface circuit 1220 may be implemented by any type of interface standard, such as an Ethernet interface, a universal serial bus (USB), and/or a PCI express interface.

One or more input devices 1222 are connected to the interface circuit 1220. The input device(s) 1222 permit a user to enter data and commands into the processor 1212. The input device(s) can be implemented by, for example, a keyboard, a mouse, a touchscreen, a track-pad, a trackball, isopoint and/or a voice recognition system.

One or more output devices 1224 are also connected to the interface circuit 1220. The output devices 1224 can be implemented, for example, by display devices (e.g., a liquid crystal display, a cathode ray tube display (CRT), etc.). The interface circuit 1220, thus, typically includes a graphics driver card.

The interface circuit 1220 also includes a communication device such as a modem or network interface card to facilitate exchange of data with external computers via a network 1226 (e.g., an Ethernet connection, a digital subscriber line (DSL), a telephone line, coaxial cable, a cellular telephone system, etc.).

The processor platform 1200 also includes one or more mass storage devices 1228 for storing software and data. Examples of such mass storage devices 1228 include floppy disk drives, hard drive disks, compact disk drives and digital versatile disk (DVD) drives. The mass storage device 1228 may implement a local storage device.

Coded instructions 1232 (e.g., coded instructions of FIGS. 3, 5-8, etc.) may be stored in the mass storage device 1228, in the volatile memory 1214, in the non-volatile memory 1216, and/or on a removable storage medium such as a CD, Blu-Ray, or DVD.

It may be noted that operations performed by the processor platform 1200 (e.g., operations corresponding to process flows or methods discussed herein, or aspects thereof) may be sufficiently complex that the operations may not be performed by a human being within a reasonable time period.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method comprising:
    receiving, using a configured processor, functional neuroimage data of a subject acquired while the subject performs a series of working memory tasks, the neuroimage data including clusters of voxels representing regions of brain activity, some regions activated and some regions deactivated during performance of the series of working memory tasks;
    extracting, using the configured processor, for a plurality of regions of interest in the neuroimage data, a mean activity level in each of the series of working memory tasks;
    determining, using the configured processor, brain activation based on the cluster of voxels corresponding to each of the plurality of regions of interest, the brain activation for each region of interest identified as a feature;
    reducing, using the configured processor, the features using a sparse principal component analysis to generate a number of orthogonal principal components smaller than the number of original features, each of the principal components corresponding to a combination of features;
    applying, using the configured processor, a logistic regression classification to the principal components based on a classification model for Attention Deficit and Hyperactivity Disorder (ADHD);
    outputting, using the configured processor, a predicted probability of ADHD based on the logistic regression classification.

2. The method as defined in claim 1, wherein functional neuroimaging comprises functional magnetic resonance imaging.

3. The method as defined in claim 1, wherein updated functional neuroimages are provided to the sparse logistic regression classification.

4. The method as defined in claim 1, wherein the working memory tasks comprise visuospatial working memory tasks.

5. The method as defined in claim 1, wherein the mean activity level for each of the series of working memory tasks is determined in comparison to a fixation task.

6. The method as defined in claim 1, wherein the series of working memory tasks include: a large-reward with no-feedback task, a large-reward with feedback task, a small-reward with no-feedback task, and a small-reward with feedback task.

7. The method as defined in claim 1, wherein determining brain activation includes analyzing brain regions with greater than a threshold of activation or deactivation compared to brain regions with less than the threshold of activation or deactivation.

8. The method as defined in claim 1, wherein the number of brain regions is sixteen, the number of working memory tasks is four, the number of features is sixty-four, and the number of principal components is ten.

9. The method as defined in claim 1, wherein the principal components are identified from the features having an eigenvalue greater than two.

10. The method as defined in claim 1, further comprising generating the classification model for ADHD based on a sample of verified ADHD subjects in comparison to normal subjects.

11. A non-transitory tangible machine readable medium having instructions stored thereon, which when executed, cause a machine to implement a method, the method comprising:
    receiving functional neuroimage data of a subject acquired while a subject performs a series of working memory tasks, the neuroimage data including clusters of voxels representing regions of brain activity, some regions activated and some regions deactivated during performance of the series of working memory tasks;
    extracting, for a plurality of regions of interest in the neuroimage data, a mean activity level in each of the series of working memory tasks;
    determining brain activation based on the cluster of voxels corresponding to each of the plurality of regions of interest, the brain activation for each region of interest identified as a feature;
    reducing the features using a sparse principal component analysis to generate a number of orthogonal principal components less than the number of features, the principal components corresponding to a combination of features;
    applying a logistic regression classification to the principal components based on a classification model for Attention Deficit and Hyperactivity Disorder (ADHD);
    outputting a predicted probability of ADHD based on the logistic regression classification.

12. The non-transitory machine readable medium as defined in claim 11, wherein functional neuroimaging comprises functional magnetic resonance imaging.

13. The non-transitory machine readable medium as defined in claim 11, wherein updated functional neuroimages are provided to the sparse logistic regression classification.

14. The non-transitory machine readable medium as defined in claim 11, wherein the working memory tasks comprise visuospatial working memory tasks.

15. The non-transitory machine readable medium as defined in claim 11, wherein the mean activity level for each of the series of working memory tasks is determined in comparison to a fixation task.

16. The non-transitory machine readable medium as defined in claim 11, wherein the series of working memory tasks include: a large-reward with no-feedback task, a large-reward with feedback task, a small-reward with no-feedback task, and a small-reward with feedback task.

17. The non-transitory machine readable medium as defined in claim 11, wherein determining brain activation includes analyzing brain regions with greater than a threshold of activation or deactivation compared to brain regions with less than the threshold of activation or deactivation.

18. The non-transitory machine readable medium as defined in claim 11, wherein the number of brain regions is sixteen, the number of working memory tasks is four, the number of features is sixty-four, and the number of principal components is ten.

19. The non-transitory machine readable medium as defined in claim 11, wherein the principal components are identified from the features having an eigenvalue greater than two.

20. The non-transitory machine readable medium as defined in claim 11, wherein the method further comprises generating the classification model for ADHD based on a sample of verified ADHD subjects in comparison to normal subjects.

\* \* \* \* \*